US012768921B2

(12) United States Patent
Ma et al.

(10) Patent No.: US 12,768,921 B2
(45) Date of Patent: Oct. 20, 2026

(54) TIME-RESOLVED IMAGE RECONSTRUCTION USING JOINT TEMPORALLY LOCAL AND GLOBAL SUBSPACE MODELING FOR MRI

(71) Applicant: Case Western Reserve University, Cleveland, OH (US)

(72) Inventors: Dan Ma, Solon, OH (US); Zhilang Qiu, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 171 days.

(21) Appl. No.: 18/643,685

(22) Filed: Apr. 23, 2024

(65) Prior Publication Data

US 2024/0361412 A1 Oct. 31, 2024

Related U.S. Application Data

(60) Provisional application No. 63/499,161, filed on Apr. 28, 2023.

(51) Int. Cl.
*G01V 3/00* (2006.01)
*A61B 5/055* (2006.01)
(Continued)

(52) U.S. Cl.
CPC .......... *G01R 33/5608* (2013.01); *A61B 5/055* (2013.01); *G01R 33/56341* (2013.01);
(Continued)

(58) Field of Classification Search
CPC .......... G01R 33/5608; G01R 33/56341; G01R 33/565; A61B 5/055; G06T 3/40; G06T 11/005
(Continued)

(56) References Cited

U.S. PATENT DOCUMENTS 8,723,518 B2 5/2014 Seiberlich et al.
2011/0148410 A1* 6/2011 Zaitsev .............. G01R 33/5611 324/309

(Continued)

FOREIGN PATENT DOCUMENTS

| | | | | |
|---|---|---|---|---|
| CA | 2833620 A1 * | 10/2012 | ........... | G01R 33/385 |
| EP | 3425416 A1 * | 1/2019 | ........... | G01R 33/561 |
| WO | WO-2015164825 A1 * | 10/2015 | ......... | G01R 33/5608 |

OTHER PUBLICATIONS

Afzali, Maryam, et al. "MR fingerprinting with b-tensor encoding for simultaneous quantification of relaxation and diffusion in a single scan." Magnetic resonance in medicine 88.5 (2022): 2043-2057.

(Continued)

*Primary Examiner* — Walter L Lindsay, Jr.
*Assistant Examiner* — Frederick Wenderoth
(74) *Attorney, Agent, or Firm* — Quarles & Brady LLP

(57) ABSTRACT

A method for reconstructing images using a self-calibrated subspace reconstruction includes receiving data acquired from a subject using a magnetic resonance imaging (MRI) system, generating aliasing-free low resolution images from at least a portion of the received data using temporally local low-rank matrix completion, estimating a temporally global subspace using the aliasing-free low resolution images, and generating aliasing-free high resolution images from the received data using temporally global subspace reconstruction that utilizes the estimated temporally global subspace. In some embodiments, a customized outlier detection algorithm can then be used to detect measurement errors in the aliasing-free high resolution images and to correct the aliasing-free high resolution images. Aliasing-free $T_1$, $T_2$, and ADC maps may be generated after comparing the (Continued)

corrected aliasing free high resolution images with a dictionary.

20 Claims, 13 Drawing Sheets

(51) Int. Cl.
*G01R 33/56* (2006.01)
*G01R 33/563* (2006.01)
*G01R 33/565* (2006.01)
*G06T 3/40* (2006.01)
*G06T 12/10* (2026.01)

(52) U.S. Cl.
CPC .............. *G01R 33/565* (2013.01); *G06T 3/40* (2013.01); *G06T 12/10* (2026.01); *G06T 2210/41* (2013.01)

(58) Field of Classification Search
USPC .......................................................... 324/309
See application file for complete search history.

(56) References Cited

U.S. PATENT DOCUMENTS

2015/0301141 A1 10/2015 Griswold et al.
2021/0298683 A1* 9/2021 Jung ...................... A61B 5/725
2022/0349971 A1 11/2022 Ma et al.

OTHER PUBLICATIONS

Candes, Emmanuel, and Benjamin Recht. "Exact matrix completion via convex optimization." Communications of the ACM 55.6 (2012): 111-119.
Cao, Xiaozhi, et al. "3D Diffusion-prepared MRF (3DM) with cardiac gating for rapid high resolution wholebrain T1, T2, proton density and diffusivity mapping." Proceedings of the Joint Annual Meeting ISMRM-ESMRMB & ISMRT 31st Annual Meeting. 2022.
Dai, Erpeng, Merry Mani, and Jennifer A. McNab. "Multi-band multi-shot diffusion MRI reconstruction with joint usage of structured low-rank constraints and explicit phase mapping." Magnetic Resonance in Medicine 89.1 (2023): 95-111.
Doneva, Mariya, et al. "Matrix completion-based reconstruction for undersampled magnetic resonance fingerprinting data." Magnetic resonance imaging 41 (2017): 41-52.
Jeong, Eun-Kee, Seong-Eun Kim, and Dennis L. Parker. "High-resolution diffusion-weighted 3D MRI, using diffusion-weighted driven-equilibrium (DW-DE) and multishot segmented 3D-SSFP without navigator echoes." Magnetic Resonance in Medicine: An Official Journal of the International Society for Magnetic Resonance in Medicine 50.4 (2003): 821-829.
Liang, Zhi-Pei. "Spatiotemporal imagingwith partially separable functions." 2007 4th IEEE international symposium on biomedical imaging: from nano to macro. IEEE, 2007.
Lu, Lan, et al. "Diffusion-prepared fast imaging with steady-state free precession (DP-FISP): a rapid diffusion MRI technique at 7 T." Magnetic resonance in medicine 68.3 (2012): 868-873.
Ma, Dan, et al. "Magnetic resonance fingerprinting." Nature 495. 7440 (2013): 187-192.
Ma, Sen, et al. "Three-dimensional simultaneous brain T1, T2, and ADC mapping with MR multitasking." Magnetic resonance in medicine 84.1 (2020): 72-88.
Mani, Merry, et al. "Multi-shot sensitivity-encoded diffusion data recovery using structured low-rank matrix completion (Mussels)." Magnetic resonance in medicine 78.2 (2017): 494-507.
Nguyen, Christopher, et al. "In vivo three-dimensional high resolution cardiac diffusion-weighted MRI: a motion compensated diffusion-prepared balanced steady-state free precession approach." Magnetic resonance in medicine 72.5 (2014): 1257-1267.
Tamir, Jonathan I., et al. "Computational MRI with physics-based constraints: Application to multicontrast and quantitative imaging." IEEE signal processing magazine 37.1 (2020): 94-104.
Porter, David A., and Robin M. Heidemann. "High resolution diffusion-weighted imaging using readout-segmented echo-planar imaging, parallel imaging and a two-dimensional navigator-based reacquisition." Magnetic Resonance in Medicine: An Official Journal of the International Society for Magnetic Resonance in Medicine 62.2 (2009): 468-475.
Jeong, Ha-Kyu, John C. Gore, and Adam W. Anderson. "High-resolution human diffusion tensor imaging using 2-D navigated multishot Sense EPI at 7 T." Magnetic resonance in medicine 69.3 (2013): 793-802.
Liu, Chunlei, et al. "Self-navigated interleaved spiral (SNAILS): application to high-resolution diffusion tensor imaging." Magnetic Resonance in Medicine: An Official Journal of the International Society for Magnetic Resonance in Medicine 52.6 (2004): 1388-1396.
Chen, Nan-kuei, et al. "A robust multi-shot scan strategy for high-resolution diffusion weighted MRI enabled by multiplexed sensitivity-encoding (MUSE)." Neuroimage 72 (2013): 41-47.
Dong, Zijing, et al. "SNR-efficient distortion-free diffusion relaxometry imaging using accelerated echo-train shifted echo-planar time-resolving imaging (ACE-EPTI)." Magnetic Resonance in Medicine 88.1 (2022): 164-179.
Gao, Y. U., et al. "Multishot diffusion-prepared magnitude-stabilized balanced steady-state free precession sequence for distortion-free diffusion imaging." Magnetic Resonance in Medicine 81.4 (2019): 2374-2384.
Fushimi, Yasutaka, et al. "Estimation of the timing of carotid artery flow using peripheral pulse wave-gated MRI." Journal of Magnetic Resonance Imaging 36.2 (2012): 454-458.
Donoho, David L. "Compressed sensing." IEEE Transactions on information theory 52.4 (2006): 1289-1306.
Candès, Emmanuel J., and Michael B. Wakin. "An introduction to compressive sampling." IEEE signal processing magazine 25.2 (2008): 21-30.
Fessler, Jeffrey A., and Bradley P. Sutton. "Nonuniform fast Fourier transforms using min-max interpolation." IEEE transactions on signal processing 51.2 (2003): 560-574.
Zhao, Bo, et al. "Improved magnetic resonance fingerprinting reconstruction with low-rank and subspace modeling." Magnetic resonance in medicine 79.2 (2018): 933-942.
Assländer, Jakob, et al. "Low rank alternating direction method of multipliers reconstruction for MR fingerprinting." Magnetic resonance in medicine 79.1 (2018): 83-96.
Weigel, Matthias. "Extended phase graphs: dephasing, RF pulses, and echoes-pure and simple." Journal of Magnetic Resonance Imaging 41.2 (2015): 266-295.
Cai, Jian-Feng, Emmanuel J. Candès, and Zuowei Shen. "A singular value thresholding algorithm for matrix completion." SIAM Journal on optimization 20.4 (2010): 1956-1982.
McGivney, Debra F., et al. "SVD compression for magnetic resonance fingerprinting in the time domain." IEEE transactions on medical imaging 33.12 (2014): 2311-2322.
Hager, William W., and Hongchao Zhang. "A survey of nonlinear conjugate gradient methods." Pacific journal of Optimization 2.1 (2006): 35-58.
Jiang, Yun, et al. "MR fingerprinting using fast imaging with steady state precession (FISP) with spiral readout." Magnetic resonance in medicine 74.6 (2015): 1621-1631.
Trzasko, Joshua, Armando Manduca, and Eric Borisch. "Local versus global low-rank promotion in dynamic MRI series reconstruction." Proc. Int. Symp. Magn. Reson. Med. vol. 19. 2011.
Zhang, Tao, John M. Pauly, and Ives R. Levesque. "Accelerating parameter mapping with a locally low rank constraint." Magnetic resonance in medicine 73.2 (2015): 655-661.
Cao, Xiaozhi, et al. "Robust sliding-window reconstruction for Accelerating the acquisition of MR fingerprinting." Magnetic resonance in medicine 78.4 (2017): 1579-1588.
Feng, Li, et al. "Golden-angle radial sparse parallel MRI: combination of compressed sensing, parallel imaging, and golden-angle

(56) References Cited

OTHER PUBLICATIONS radial sampling for fast and flexible dynamic volumetric MRI." Magnetic resonance in medicine 72.3 (2014): 707-717.
Jacob, Mathews, Merry P. Mani, and Jong Chul Ye. "Structured low-rank algorithms: Theory, magnetic resonance applications, and links to machine learning." IEEE signal processing magazine 37.1 (2020): 54-68.
Bustin, Aurélien, et al. "High-dimensionality undersampled patch-based reconstruction (HD-PROST) for accelerated multi-contrast MRI." Magnetic resonance in medicine 81.6 (2019): 3705-3719.
Feng, Li. "4D golden-angle radial MRI at subsecond temporal resolution." NMR in Biomedicine 36.2 (2023): e4844.

* cited by examiner

TIME-RESOLVED IMAGE RECONSTRUCTION USING JOINT TEMPORALLY LOCAL AND GLOBAL SUBSPACE MODELING FOR MRI

CROSS-REFERENCE TO RELATED APPLICATIONS

This application is based on, claims priority to, and incorporates herein by reference in its entirety U.S. Ser. No. 63/499,161 filed Apr. 28, 2023, and entitled "Time-Resolved Image Reconstruction Using Joint Temporally Local and Global Subspace Modeling for Diffusion MRI."

STATEMENT REGARDING FEDERALLY SPONSORED RESEARCH

This invention was made with government support under grant numbers CA269604 and NS109439 awarded by the National Institutes of Health. The government has certain rights in the invention.

BACKGROUND

Magnetic resonance (MR) imaging (MRI) is a biomedical imaging technology to form pictures of the anatomy and the physiological processes of the body. Diffusion MRI is an MRI technique that measures the diffusion process of water molecules in tissues. Diffusion MRI determines the contrast mechanism by the diffusion process, which characterizes the Brownian motion of water molecules in tissues. In diffusion MRI, diffusion-weighted images are acquired and/or the diffusion parametric (e.g., apparent diffusion coefficient, ADC) maps are measured from multiple images with differential diffusion weightings. A common issue in diffusion MRI is that measurement errors induced by physiological motion, bulk motion, and eddy currents during diffusion encoding can result in artifacts in reconstructed diffusion weighted images and parametric maps. To reduce distortion and blurring effects, diffusion MRI usually employs a segmented acquisition strategy to acquire k-space data, also known as multi-shot acquisition, which involves repeating multiple data acquisitions, each starting with a diffusion preparation module, to form the whole k-space. However, inter-shot (i.e., shot-to-shot) phase variation induced by physiological motion (e.g., cardiac pulsation), bulk motion, and eddy currents during diffusion encoding can cause artifacts in reconstructed images and diffusion maps when combining the data from all shots to reconstruct an image without accounting for the inter-shot phase variation.

Many reconstruction methods have been proposed to address the issue presented by measurement errors retrospectively. These methods can be divided into two categories based on the principle of modeling. The first category is phase-corrected model-based reconstruction, where the inter-shot phase variation is characterized by explicit phase maps, which are obtained and then fed into the phase-corrected model-based reconstruction. Typically, the explicit phase maps are estimated from low-resolution images acquired by an extra navigator or self-navigator reconstructed from the densely sampled k-space center for each shot. A second category of reconstruction methods that can be used to address the issue presented by measurement errors retrospectively is subspace- or matrix completion-based reconstruction, which implicitly captures the inter-shot phase variation and explores global data sharing (i.e., data correlation across all shots) using a subspace and has the advantage of high robustness. In particular, a subspace reconstruction method is computation- and memory-efficient for time-resolved image reconstruction where images are reconstructed for each time or readout. However, extra calibration data is usually needed to pre-estimate a data-driven temporal subspace in conventional subspace reconstruction methods for time-resolved images reconstruction. Acquisition of the calibration data can cost extra scan time. Matrix completion can be used to eliminate the need for extra calibration data but encounters a challenge that the commonly used temporally global matrix completion is not applicable because of weakened low-rank assumption due to measurement errors.

Recently, several quantitative MRI techniques have been developed to simultaneously quantify relaxation and diffusion from a single scan, such as multidimensional MR Fingerprinting (mdMRF). mdMRF employs a sequence structure consisting of multiple segments (or blocks) with each segment starting with a preparation module (e.g., inversion for T1 preparation, T2 preparation, or diffusion preparation), followed by continuous and time-resolved image acquisition, and ending with a waiting time, making the signal sensitive to both relaxation and diffusion effects. A multi-shot acquisition cam also be employed to acquire more data for each time point. However, similar to conventional diffusion MRI techniques, inter-shot/segment phase variation exists in mdMRF. Because a diffusion-prepared (DP) encoding scheme is used for diffusion encoding, intra-shot/segment (i.e., images within a shot/segment) phase variation is also present. Moreover, inter- and intra-shot/segment magnitude variations also occur in mdMRF, because stabilizer has not been used along with the DP scheme. These inter- and intra-shot/segment magnitude and phase variations can be viewed as measurement errors, which can cause corruption of the diffusion-weighted images and lead to artifacts in quantitative maps, such as ADC maps. To address such artifacts, mdMRF employs peripheral pulsation gating to mitigate the effects of cardiac pulsation during diffusion encoding and reduce the measurement errors prospectively. However, this strategy has several limitations, such as longer scan time due to skipped pulsation triggers and a much-reduced efficiency in reconstruction or mapping due to the need to generate a dictionary after each specific scan.

SUMMARY OF THE DISCLOSURE

In accordance with an embodiment, a method for reconstructing images using a self-calibrated subspace reconstruction includes receiving data acquired from a subject using a magnetic resonance imaging (MRI) system, generating aliasing-free low resolution images from at least a portion of the received data using temporally local low-rank matrix completion, estimating a temporally global subspace using the aliasing-free low resolution images, and generating aliasing-free high resolution images from the received data using temporally global subspace reconstruction that utilizes the estimated temporally global subspace.

In accordance with another embodiment, a magnetic resonance imaging (MRI) system includes a magnet system configured to generate a polarizing magnetic field about a portion of a subject positioned, a magnetic gradient system including a plurality of magnetic gradient coils configured to apply at least one magnetic gradient field to the polarizing magnetic field, a radio frequency (RF) system configured to apply an RF excitation field to the subject, and to receive magnetic resonance signals from the subject using a coil array and at least one processor. The at least one processor can be configured to direct the plurality of magnetic gradient coils and the RF system to perform a pulse sequence to acquire data from a subject, generate aliasing-free low resolution images from at least a portion of the received data using temporally local low-rank matrix completion, estimate a temporally global subspace using the aliasing-free low resolution images, and generate aliasing-free high resolution images from the received data using temporally global subspace reconstruction that utilizes the estimated temporally global subspace.

In accordance with another embodiment, a non-transitory, computer readable medium storing instructions that, when executed by one or more processors, perform a set of functions is provided. The set of functions include receiving data acquired from a subject using a magnetic resonance imaging (MRI) system, generating aliasing-free low resolution images from at least a portion of the received data using temporally local low-rank matrix completion, estimating a temporally global subspace using the aliasing-free low resolution images, and generating aliasing-free high resolution images from the received data using temporally global subspace reconstruction that utilizes the estimated temporally global subspace.

BRIEF DESCRIPTION OF THE DRAWINGS

The present invention will hereafter be described with reference to the accompanying drawings, wherein like reference numerals denote like elements.

DETAILED DESCRIPTION

Figure 1:
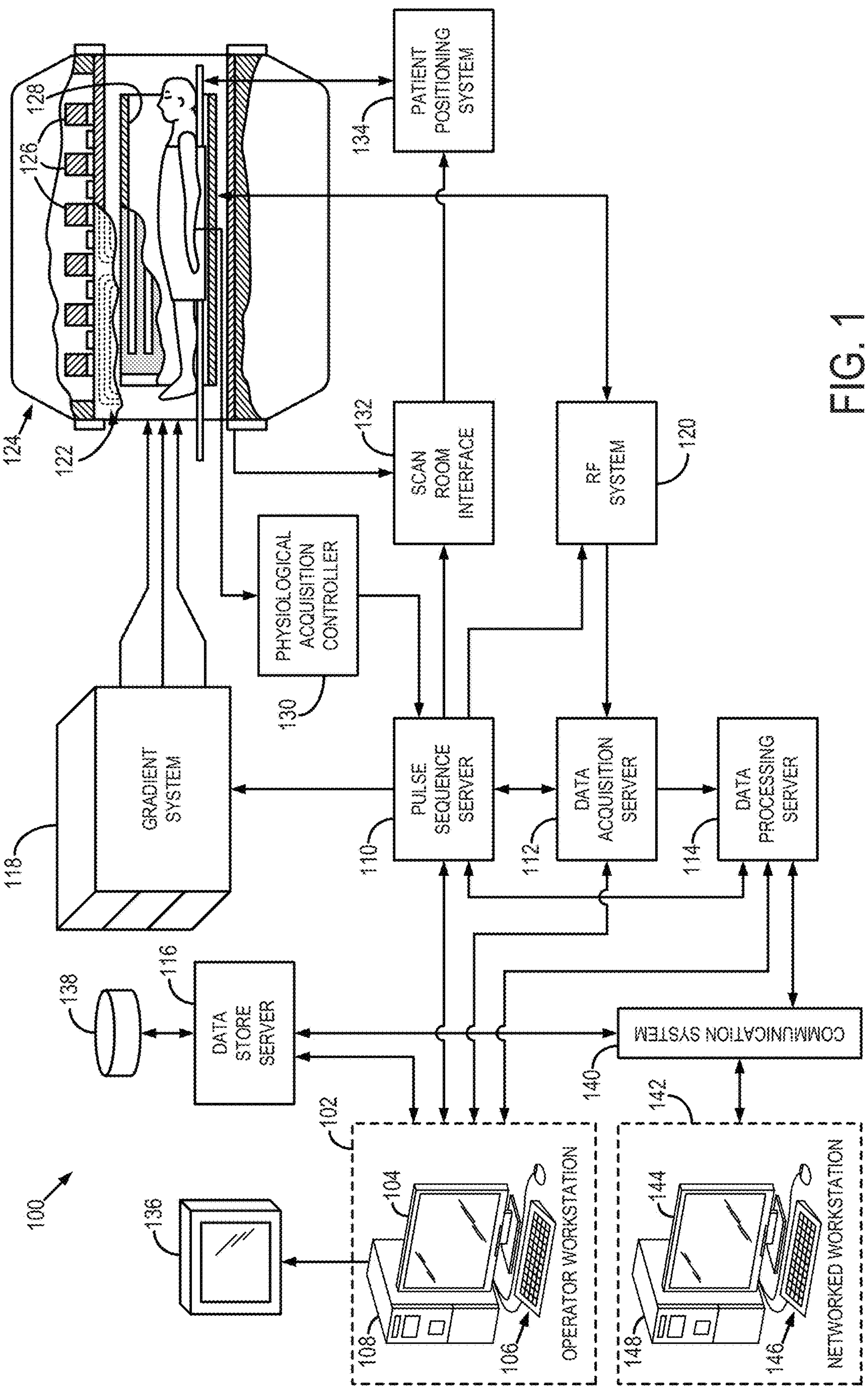
FIG. 1 is a schematic diagram of an example MRI system in accordance with an embodiment.

Magnetic resonance fingerprinting ("MRF") is a technique that facilitates mapping of tissue or other material properties based on random or pseudorandom measurements of the subject or object being imaged. In particular, MRF can be conceptualized as evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE'), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom, or may contain signals from different materials or tissues that are spatially incoherent, temporally incoherent, or both, MRF processes can be designed to map any of a wide variety of parameters or properties. Examples of such parameters or properties that can be mapped may include, but are not limited to, tissue parameters or properties such as longitudinal relaxation time ($T_1$), transverse relaxation time ($T_2$), and proton density ($\rho$), and device dependent parameters such as main or static magnetic field map ($B_0$). MRF is generally described in U.S. Pat. No. 8,723,518 and Published U.S. Patent Application No. 2015/0301141, each of which is incorporated herein by reference in its entirety.

The data acquired with MRF techniques are compared with a dictionary of signal models, or templates, which have been generated for different acquisition parameters from magnetic resonance signal models, such as Bloch equation-based physics simulations. This comparison allows estimation of the physical properties, such as those mentioned above. As an example, the comparison of the acquired signals to a dictionary can be performed using any suitable matching or pattern recognition technique. The properties for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative properties, which can be extracted from the selected signal vector and used to generate the relevant quantitative property maps.

In MRF, a unique signal timecourse is generated for each pixel. This timecourse evolves based on both physiological tissue properties such as $T_1$ or $T_2$ as well as acquisition parameters like flip angle (FA) and repetition time (TR). This signal timecourse can, thus, be referred to as a signal evolution and each pixel can be matched to an entry in the dictionary, which is a collection of possible signal evolutions or timecourses calculated using a range of possible tissue property values and knowledge of the quantum physics that govern the signal evolution. Upon matching the measured signal evolution/timecourse to a specific dictionary entry, the tissue properties corresponding to that dictionary entry can be identified. A fundamental criterion in MRF is that spatial incoherence be maintained to help separate signals that are mixed due to undersampling. In other words, signals from various locations should differ from each other, in order to be able to separate them when aliased.

To achieve this process, a magnetic resonance imaging (MRI) system or nuclear magnetic resonance (NMR) system may be utilized. FIG. 1 shows an example of an MRI system 100 that may be used to perform magnetic resonance fingerprinting. In addition, MRI system 100 may be used to implement the methods described herein. MRI system 100 includes an operator workstation 102, which may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \tag{1}$$

and the phase of the received magnetic resonance signal may also be determined according to the following relationship:

$$\varphi = \tan^{-1}\left(\frac{Q}{I}\right) \tag{2}$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heartbeat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The present disclosure describes a system and method for reconstruction of image(s) that utilizes joint temporally local and global subspace modeling, which may be referred to herein as self-calibrated subspace reconstruction. The joint subspace modeling can be implemented in a two-step manner: 1) temporally local matrix completion can be used to obtain aliasing-free and low-resolution images; 2) temporally global subspace reconstruction can be performed to reconstruct aliasing-free and high-resolution images, where the subspace may be estimated from the low-resolution images. In some embodiments, the disclosed reconstruction technique can be applied in multidimensional MR Fingerprinting (mdMRF), which is a fast quantitative imaging technique for simultaneous quantification of relaxation and diffusion, to address the measurement errors retrospectively and generate artifact-free $T_1$, $T_2$, and ADC (apparent diffusion coefficient) maps without separately acquired calibration data or prospective data. In some embodiments, the disclosed reconstruction technique can be extended to other diffusion MRI techniques.

The disclosed reconstruction technique advantageously fully utilizes the low-rank property according to the signal structure, enabling aliasing-free high-resolution image reconstruction and robust artifact correction, for example, for mdMRF. In some embodiments, the disclosed reconstruction method, also referred to herein as self-calibrated subspace reconstruction, may be used for mdMRF, in order to correct the artifacts due to inter-shot (segment) and intra-shot magnitude and phase variations, without the need for pulsation gating, extra navigator, real time calibration data, or fully sampled central k-space. Accordingly, aliasing-free high-resolution image reconstruction and high quality quantification can be achieved. While the following description is discussed in terms of using the disclosed reconstruction technique for MRF or mdMRF, it should be understood that the disclosed reconstruction technique may be used for time-resolved image reconstruction for other diffusion MRI techniques, for example, multi-shot diffusion MRI and relaxation-diffusion quantitative MRI.

The disclosed self-calibrated subspace reconstruction uses temporally local low-rank matrix completion, which takes advantage of the temporally local low-rank property of, for example, mdMRF data, to address the weakened global low-rank assumption caused by inter-shot (segment) magnitude modifications and phase variations. Advantageously, no extra navigator, real-time calibration data, or fully sampled central k-space is required. Aliasing-free high-resolution images can be reconstructed and corrected (excluded) to generate, for example, artifact-free $T_1$, $T_2$, and ADC maps.

Figure 2:
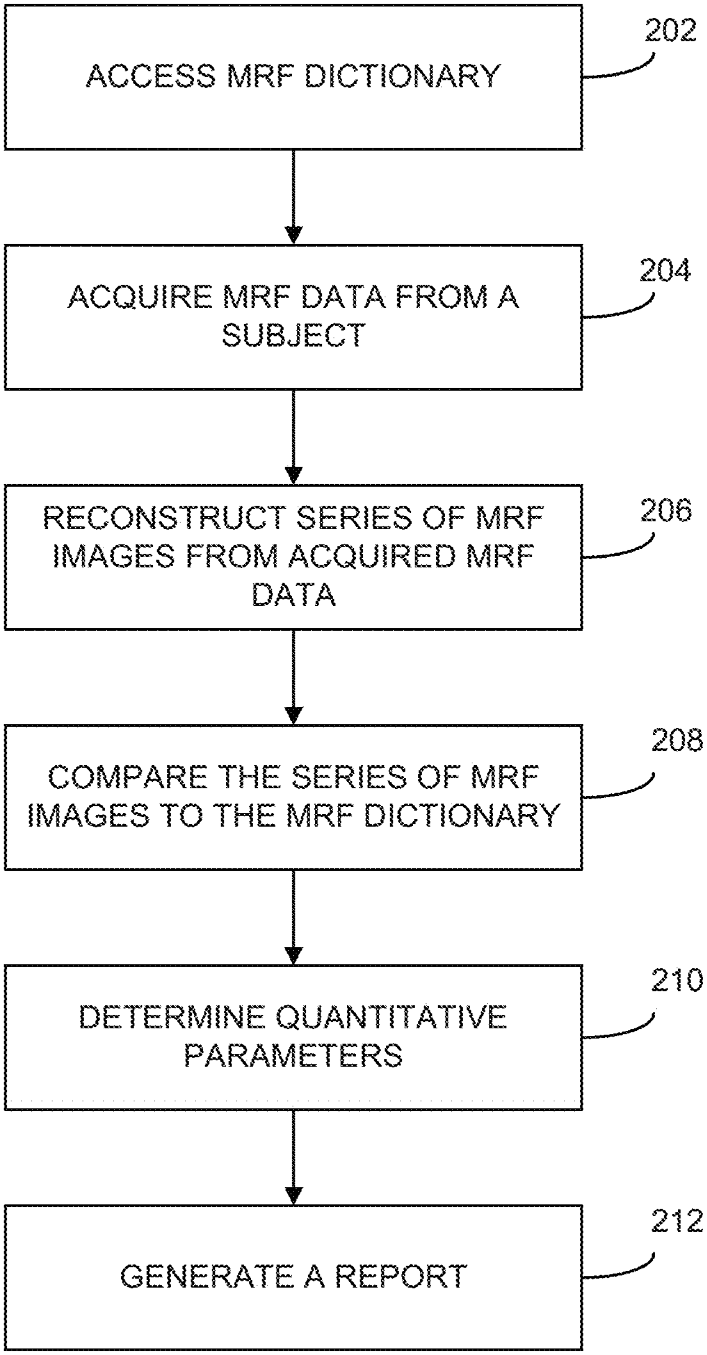
FIG. 2 illustrates an example method for magnetic resonance fingerprinting (MRF) in accordance with an embodiment.

FIG. 2 illustrates an example method for magnetic resonance fingerprinting (MRF) in accordance with an embodiment. Although the blocks of the process of FIG. 2 are illustrated on a particular order, in some embodiments, one or more blocks may be executed in a different order than illustrated in FIG. 2, or may be bypassed. At block 202, an MRF dictionary is accessed. The MRF dictionary can include known signal evolutions (e.g., simulated signal evolutions) and can include parameters and properties (e.g., quantitative parameters pr property values) associated with each signal evolution, for example, $T_1$, $T_2$, proton density, and off-resonance. For mdMRF, the parameters and properties may also include diffusivity or diffusion tensor. In some embodiments, the MRF dictionary may be generated using a Bloch simulation or Bloch-Torrey equation. In some embodiments, the MRF dictionary may be stored in memory or data storage of, for example, an MRI system (e.g., MRI system 100 shown in FIG. 1) or other computer system. As used herein, the term "accessing" may refer to any number of activities related to retrieving or processing the MRF dictionary using, for example, MRI system 100 (shown in FIG. 1), an extended network, information repository, or combinations thereof.

At block 204, MRF data may be acquired from a subject, for example, from a tissue or region of interest in a subject. The MRF data may be acquired using, for example, an MRI system (e.g., MRI system 100 shown in FIG. 1). Acquiring MRF data may include performing or playing-out a pulse sequence, for example, an MRF or mdMRF pulse sequence. An MRF acquisition can be configured to simultaneously quantify parameters such as $T_1$, $T_2$, and proton density. An mdMRF acquisition can be configured to for example, simultaneously quantify relaxation and diffusion parameters and properties, such as, for example, $T_1$, $T_2$, diffusivity or diffusion tensor, and proton density. In some embodiments, the diffusivity or diffusion tensor may be used to measure quantitative parameters such as, for example, apparent diffusion coefficient (ADC), fractional anisotropy (FA), microscopic anisotropy (μFA), or other microstructure related parameters. An example mdMRF pulse sequence and technique is described in U.S. Patent Application Publication US 2022/0349971, published Nov. 3, 2022, herein incorporated by reference in its entirety.

In some embodiments, at block 206 the MRF data may be reconstructed before comparison with the MRF dictionary at block 208. For example, in some embodiments a series of time-resolved MRF images may be reconstructed at block 206 from the acquired MRF data. In some embodiments, the MRF image(s) may be reconstructed using the disclosed self-calibrated subspace reconstruction with joint temporally local and global subspace modeling as described further below with respect to FIG. 3. The acquired MRF data and/or the reconstructed MRF images may be stored in memory or data storage of, for example, an MRI system (e.g., the MRI system 100 of FIG. 1) or other computer system.

The reconstructed MRF images from block 206 (or the MRF data acquired at bock 204) may be compared to the MRF dictionary at block 208 to match the acquired signal evolutions with signal evolutions stored in the MRF dictionary. "Match" as used herein refers to the result of comparing signals but does not refer to an exact match, which may or may not be found. A match may be the signal evolution that most closely resembles another signal evolution. Comparing the MRF data (or reconstructed images) to the MRF dictionary may be performed in a number of ways such as, for example, using a pattern matching, template matching or other matching algorithm. In some embodiments, dot product pattern matching may be used to select the MRF dictionary entry which most closely fits the acquired signal evolution to extract $T_1$. $T_2$, and diffusivity or diffusion tensor for each pixel. In some embodiments, the inner products between the normalized time course of each pixel and all entries of the normalized dictionary are calculated, and the dictionary entry corresponding to the maximum value of the inner product is taken to represent the closest signal evolution to the acquired signal evolution. In some embodiments, iterative pattern matching may be used.

At block 210, one or more quantitative parameters (e.g., relaxation and diffusion parameters) of the MRF data may be determined based on the comparison and matching at block 208. For example, based on the comparison and matching in block 208, the signal evolution (i.e., a dictionary entry) that is determined to be the closest signal evolution (or closest fit) to the acquired signal evolutions may be selected and the parameters associated with the selected dictionary entry assigned to the acquire signal evolutions. The parameters may include, for example, longitudinal relaxation time ($T_1$), transverse relaxation time ($T_2$), and, for md-MRF acquisitions, can also include diffusivity or diffusion tensor. In some embodiments, other parameters may be determined from the comparison and matching, such as, for example, main or static magnetic field ($B_0$), and proton density. In some embodiments, for an mdMRF acquisition one or more diffusion or diffusivity parameters may be determined using the parameters (e.g., diffusivity or diffusion tensor) determined from the dictionary matching at block 306. For example, in some embodiments, known methods may be used to determine quantitative parameters for mean diffusivity (MD), apparent diffusion coefficient (ADC), fractional anisotropy (FA), microscopic fractional anisotropy (μFA), or other microstructure related parameters, such as for example, axon diameters, cell density, tissue partial volume, and volume fraction, from the parameters (e.g., diffusivity or diffusion tensor) determined from the dictionary matching at block 306. In an example, the ADC may be calculated by averaging the diffusivity from three diffusion encoding directions. In another example, the fractional anisotropy may be calculated using a known model of axial diffusivity and radial diffusivity. In yet another example, the microscopic fractional anisotropy may be calculated using known methods of diffusivity. In some embodiments, the determined quantitative parameters may be stored in memory or data storage of, for example, an MRI system (e.g., MRI system 100 shown in FIG. 1) or other computer system.

At block 212, a report may be generated indicating at least one of the identified parameters (e.g., relaxation and diffusion parameters) for the tissue in a region of interest in a subject. For example, the report may include a quantitative indication of the at least one parameter. The report may include, for example, images or maps, text or metric based reports, audio reports and the like. The report may be provided to a display (e.g., display 104, 136 or 144 shown in FIG. 1). In some embodiments, the report may be stored in memory or data storage of, for example, an MRI system (e.g., MRI system 100 shown in FIG. 1) or other computer system.

Figure 3:
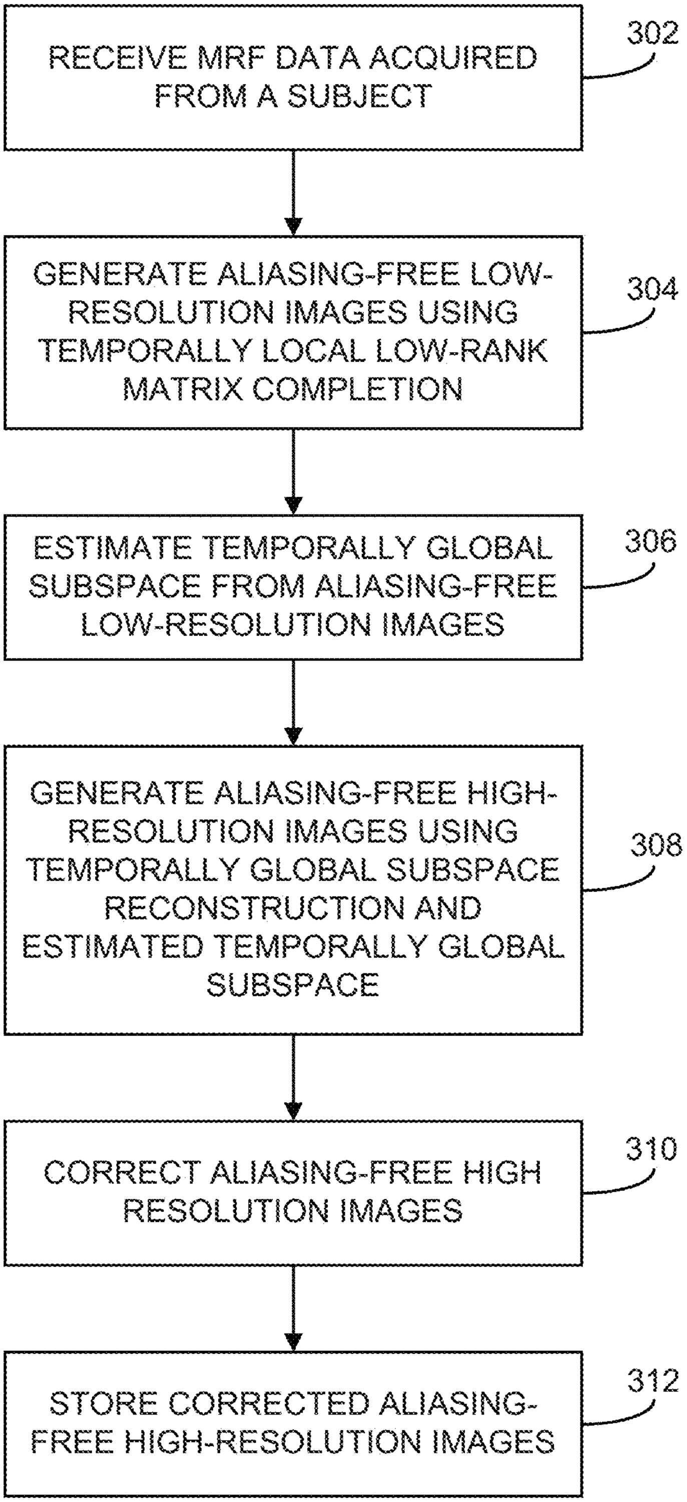
FIG. 3 illustrates a method for reconstructing MRF images using a self-calibrated subspace reconstruction in accordance with an embodiment.

FIG. 3 illustrates a method for reconstructing MRF images using a self-calibrated subspace reconstruction in accordance with an embodiment. Although the blocks of the process of FIG. 3 are illustrated in a particular order, in some embodiments, one or more blocks may be executed in a different order than illustrated in FIG. 3, or may be bypassed. At block 302, MRF data acquired from a subject (e.g., from a tissue or region of interest of the subject) may be received. The MRF data may be acquired using, for example, an MRI system (e.g., MRI system 100 shown in FIG. 1). In some embodiments, the MRF data may be retrieved from memory or data storage of, for example, an MRI system (e.g., the MRI system 100 of FIG. 1) or other computer system. In some embodiments, the MRF data may be acquired using an mdMRF pulse sequence and the MRF data is mdMRF data. While the following description of FIG. 3 will refer to mdMRF, it should be understood that, in some embodiments, the acquired data may be acquired using MRF or other diffusion MRI acquisition techniques, for example, other multi-shot diffusion MRI and relaxation-diffusion quantitative MRI techniques.

At block 304, aliasing-free low resolution images may be generated (or reconstructed) from the acquired MRF data (block 302) using temporally local low-rank matrix completion. For example, a temporally local low-rank matrix completion method may be applied on undersampled central k-space data from the acquired MRF data to reconstruct aliasing-free low-resolution images that, as discussed further below, can be used as calibration data. Accordingly, fully sampled low-resolution calibration data can be obtained from the undersampled central k-space using temporally local (segment-wise) matrix completion. In some embodiments, for example, a set of data ($d_c$) may be extracted from the central k-space (e.g., 2.5-fold resolution reduction related to the full k-space) of the under-sampled imaging data ($d_u$) received at block 302 (e.g., the MRF data acquired from a subject), and then a sliding window (e.g., size=5) may be used to form a denser under-sampled central k-space ($\hat{d}_c$). The 2.5-fold resolution reduction and a sliding window size of 5 are given as examples and it should be understood that in some embodiments, these values can be extended to other reasonable numbers. Temporally local matrix completion, which performs matrix completion for each segment, may be used to reconstruct the aliasing-free and low-resolution images ($\hat{m}_c$) from $\hat{d}_c$. As described above, the commonly used temporally global matrix completion is not applicable because the temporally global low-rank property is weakened by the measurement errors caused by motion or eddy currents. The global low-rank property can be weakened by inter-shot phase variation. On the other hand, in a segmented acquisition, e.g., an mdMRF scan, where the duration of each segment is less than, for example, 500 ms, the temporally local low-rank property, i.e., the low-rank assumption for the imaging data of each segment, is highly satisfied. Therefore, the self-calibrated subspace reconstruction can advantageously utilize temporally local matrix completion to reconstruct aliasing-free low-resolution images. The reconstruction model may be given by:

$$\hat{m}_c = \underset{m_c}{\operatorname{argmin}} \left\|\hat{d}_c - \Omega F S_c m_c\right\|_2^2 + \lambda_l \sum\nolimits_{s=1}^{N_s} \|m_{c,s}\|_* \tag{3}$$

where $S_c$ is the low-resolution coil sensitivity estimated from fully sampled data by combining $\hat{d}_c$ along the time dimension, F and Ω denote the Fourier encoding in the spatial domain and under-sampling mask in k-t domain, respectively, $m_c$ is the low-resolution image series (x-t domain) to be reconstructed, $m_{c,s}$ is a portion of $m_c$ corresponding to s-th segment, $N_s$ is the number of segments and $\lambda_l$ is the regularization parameter. In some embodiments, the iterative shrinkage-thresholding (ISTA) algorithm may be used to solve the problem of equation 3. In some embodiments, other algorithms that may be used to solve the problem of equation 3 can include, for example, FISTA, ADMM, etc. In some embodiments, the aliasing-free low-resolution images reconstructed at block 304 may be stored in memory or data storage of, for example, an MRI system (e.g., MRI system 100 shown in FIG. 1) or other computer system.

At block 306, a temporally global subspace is estimated from the aliasing-free low-resolution images (i.e., fully sampled low resolution calibration data) generated at block 304. In some embodiments, the temporally global subspace (V) may be estimated by performing singular value decomposition (SVD) and truncation (<1% error) on the low-resolution images obtained at block 304. In some embodiments, the temporally global subspace may be stored in memory or data storage of, for example, an MRI system (e.g., MRI system 100 shown in FIG. 1) or other computer system.

At block 308, aliasing-free high-resolution may be generated (or reconstructed) using temporally global subspace reconstruction and the subspace estimated at block 306. Because the low-resolution and high-resolution MRF (or mdMRF) data share the same temporal subspace, temporally global subspace reconstruction may be used to reconstruct high-resolution images from the undersampled full k-space (e.g., the MRF data received at block 302), where the subspace is estimated from the calibration data (i.e., the low resolution images) obtained at block 304. Subspace reconstruction is essentially a linear reconstruction exploring a low-dimensional signal structure given the subspace known and the performance and subspace reconstruction may greatly benefit from more data sharing. In some embodiments, temporally global subspace reconstruction may be used to reconstruct aliasing-free and high-resolution images ($\hat{m}$), including the corrupted and non-corrupted images, from the highly undersampled imaging data $d_u$ (e.g., the acquired MRF data received at block 302 that represents undersampled whole or full k-space). The joint subspace modeling may be implemented sequentially. As low-resolution images have been reconstructed at block 304, both temporally local and temporally global subspace can be estimated from the low-resolution images. In principle, both temporally local and temporally global subspace reconstruction can be used to reconstruct aliasing-free and high-resolution images. However, because subspace reconstruction benefits from more data sharing, i.e., exploring the correlation between more data, temporally global subspace would achieve much-improved image quality because of global data sharing, compared to temporally local subspace reconstruction. Hence, the disclosed self-calibrated subspace reconstructions method advantageously uses temporally global subspace reconstruction to reconstruct aliasing-free and high-resolution images at block 308. In some embodiments, the reconstruction model may be given by:

$$\hat{U} = \underset{U}{\operatorname{argmin}} \| d_u - \Omega F S U V^H \|_2^2 + \lambda \mathcal{R}(U) \tag{4}$$

where S is the high-resolution coil sensitivity estimated from fully sampled data by combining $d_u$ along the time dimension, and U denotes the coefficient images to be reconstructed, i.e., image series in spatial and SVD compressed temporal domain. Aliasing-free and high-resolution images $\hat{m}$ (x-t domain) can be finally formed by $\hat{U}V^H$. In equation 4, $\mathcal{R}$ denotes the additional sparsity constraint and λ is the regularization parameter. In some embodiments, a nonlinear conjugate gradient (NLCG) algorithm may be used to solve the problem in equation 4. In some embodiments, other algorithms that may be used to solve the problem in equation 4 can include, for example, conjugate gradient (CG), ISTA, FISTA, ADMM, etc. In some embodiments, the aliasing-free high-resolution images generated at block 308 may be stored in memory or data storage of, for example, an MRI system (e.g., the MRI system 100 of FIG. 1) or other computer system.

The aliasing-free high resolution images reconstructed at block 308 can include errors, i.e., the reconstructed aliasing-free high resolution images can include corrupted and non-corrupted images (or segments). At block 310, the errors in the high resolution images may be detected and corrected, for example, the detected errors may be excluded. In some embodiments, the corrupted segments, i.e., the segments with corrupted images contaminated by measurement errors, can be detected using a known outlier detection algorithm or a customized outlier detection algorithm. Although the reconstructed low-resolution images from block 304 can also be used to identify measurement error-corrupted images, it may be advantageous to use the high-resolution images from block 308, because they are of higher image quality, which enables automatic and robust measurement error detection. In some embodiments, the measurement error detection algorithm may be based on the observation that the phase errors are more apparent in the first few images right after the diffusion preparation in the affected segments. In the last few images of those segments, where the diffusion sensitivity decreases and the signal is mainly governed by $T_1$ recovery, the phase errors are negligible.

Figure 4:
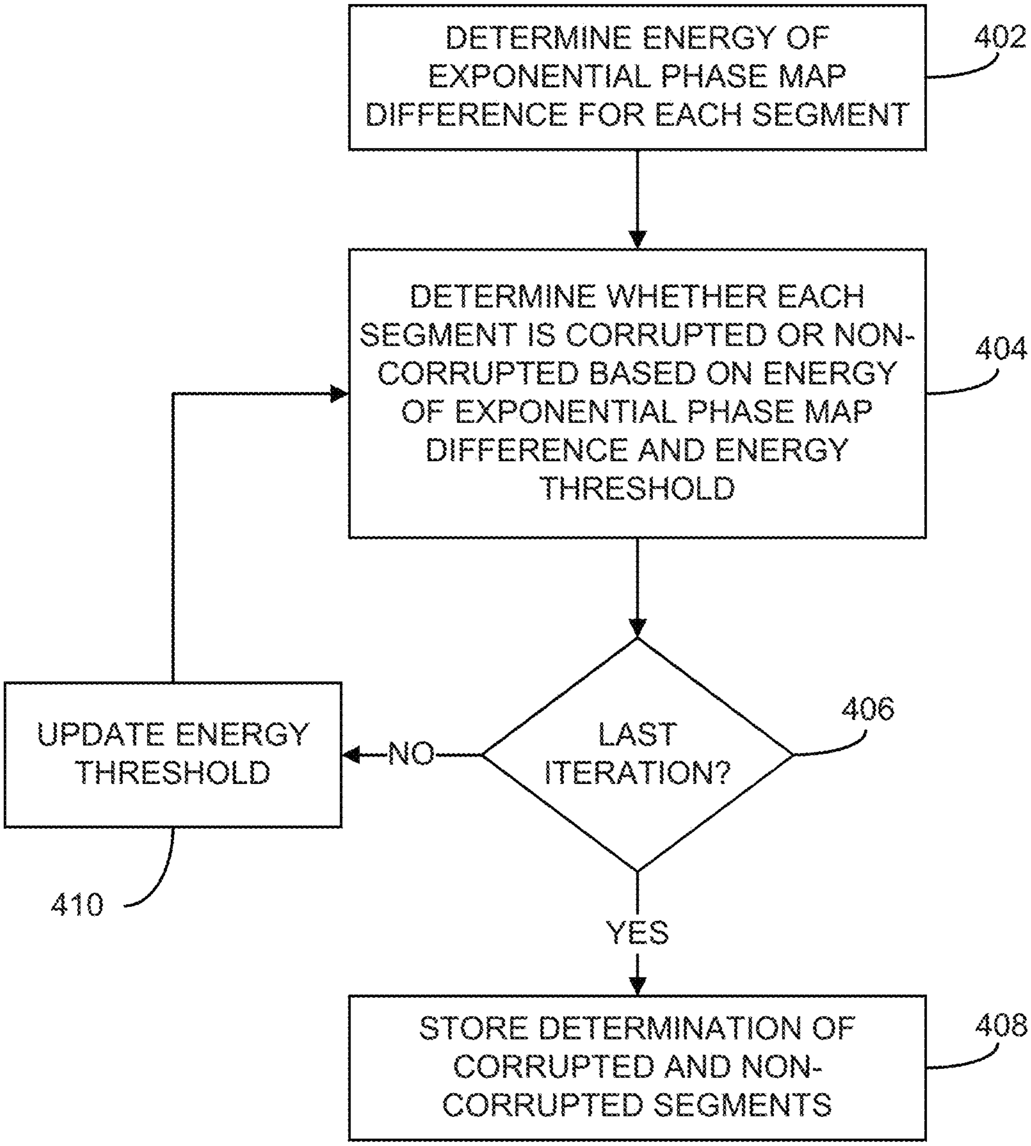
FIG. 4 illustrates an example method for measurement error detection in accordance with an embodiment.

For example, FIG. 4 illustrates an example method for measurement error detection in accordance with an embodiment. As mentioned, in some embodiments, the measurement error detection method can use an example customized outlier detection algorithm. At block 402, an energy of the exponential phase map difference, $E_s$, can be calculated for each segment, s, of the reconstructed images. For example, for each segment, unit-magnitude phase maps ( $$m_1^s$$

and $$m_e^s$$

) may be extracted from the first and the last images of the segment. Then, the energy of the phase map difference ($E_s$) may be calculated for the segment by taking the difference between the unit magnitude phase maps. In some embodiments, the energy of the phase map difference ($E_s$) may be given by:

$$E_s = \|m_1^s - m_e^s\|_2^2 \tag{5}$$

where s=1, 2, . . . , $N_{seg}$. At block 404, it can be determined whether each segment is corrupted (e.g., an outlier) or non-corrupted. In some embodiments, whether a segment s corrupted or non-corrupted can be determined based on the energy of the phase map different, $E_s$, for the segment and a threshold value, $E_{thresh}$. For example, in some embodiments, based on the assumption that the corrupted segments can have higher energies because of phase variation, while the non-corrupted segments can have lower energies, the segments can be iteratively clustered into two groups in terms of $E_s$: one for corrupted segments ($\Omega_{corr}$) and the other for non-corrupted segments ($\Omega_{noncorr}$). For example, $E_s$ can be compared to the threshold value ($E_{thresh}$), as given by:

$$\Omega_{corr} = \{s \mid E_s > E_{thresh}\} \tag{6}$$

$$\Omega_{noncorr} = \{s \mid E_s \le E_{thresh}\} \tag{7}$$

In some embodiments, in each iteration, k, the energy threshold ($E_{thresh}$) may be determined by the average energy of the non-corrupted segments $\Omega_{noncorr}$ in the previous iteration, as given by:

$$E_{thresh} = \eta \cdot \mathrm{mean}\{E_s \mid s \in \Omega_{noncorr}^k\} \tag{8}$$

Where η is an empirical coefficient that scales the mean value of {

$$E_s \mid s \in \Omega_{noncorr}^k$$

} to update $E_{thresh}$. The segments with higher energies may be clustered into $\Omega_{corr}$, while the segments with lower energies may be clustered into $\Omega_{noncorr}$. Accordingly, in some embodiments, the corrupted segments can be detected automatically as having higher energies than the non-corrupted segments. For the example clustering process, in the first iteration, the various variables including the threshold value, $E_{thresh}$, can be initialized, for example, as given by:

$$\eta = 2.5 \tag{9}$$

$$\Omega_{corr}^0 = \phi \tag{10}$$

$$\Omega_{noncorr}^0 = \{1, 2, \ldots \ldots, N_{seg}\} \tag{11}$$

$$E_{thresh}^0 = \eta \cdot \mathrm{mean}\{E_s \mid s \in \Omega_{noncorr}\} \tag{12}$$

Accordingly, the initial threshold value, $E_{thresh}$, for the first iteration may be determined based on the average energy of all of the segments based on the initialization value that all of the segments fall into the non-corrupted group. At block 406, it can be determined whether it is the last iteration of the clustering process, for example, based on whether an end condition has been met. For example, the clustering process may end if the current group of non-corrupted segments for the current iteration, $$\Omega_{noncorr}^k,$$

is the same as the group of non-corrupted segments for the prior segment, $$\Omega_{noncorr}^{k-1},$$

as given by:

$$\{\Omega_{noncorr}^k == \Omega_{noncorr}^{k-1}\} \tag{13}$$

If it is not the last iteration, i.e., the end condition as given by Equation 13 is not met, the process moves to block 410 and a new threshold value, $E_{thresh}$, is determined based on the energy, $E_s$, for each of the segments included in the non-corrupted group based on the clustering process of the previous iteration. The process then returns to block 404 and the segments are clustered into corrupted segments ($\Omega_{corr}$) non-corrupted segments ($\Omega_{noncorr}$) based on the energies, $E_s$, determined for each segment at block 402 and the updated threshold value determined at block 410.

At block 406, if it is determined that it is the last iteration, i.e., the end condition as given by Equation 13 is met, then the process moves to block 408. At block 408, the determination (e.g., the groupings) of corrupted and non-corrupted segments for the current iteration can be stored in memory or data storage of, for example, an MRI system (e.g., the MRI system 100 of FIG. 1) or other computer system.

Returning to block 310 of FIG. 3, as mentioned above, once the errors (or corrupted segments/images) in the reconstructed aliasing-free high resolution images have been detected, the errors may be corrected, for example, by excluding the corrupted segments. In some embodiments for mdMRF, because the corrupted images or segments contain both magnitude and phase variations, correcting the phase alone (while keeping the magnitude), which is used commonly in other diffusion MRI techniques, is not applicable in mdMRF. Because the magnitude variation is mixed with physical processes (e.g., T1 recovery and T2 decay) and is hard to distinguish, in some embodiments for mdMRF, a simple correction strategy may be performed by directly excluding the detected corrupted segments.

At block 312, the corrected aliasing-free high-resolution images generated at block 310 may be stored in memory or data storage of, for example, an MRI system (e.g., the MRI system 100 of FIG. 1) or other computer system. In some embodiments, the aliasing free high resolution images reconstructed using the disclosed self-calibrated subspace reconstruction discussed with respect to FIG. 3 may be time-resolved images that may be used for quantification of relaxation and/or diffusion. In some embodiments, the aliasing-free high resolution images may be a series of time resolved MRF images and may be used in an MRF or mdMRF process for determining quantitative parameters by comparing the reconstructed images to an MRF dictionary. In some embodiments, once the aliasing-free high resolution images are corrected (e.g., the corrupted segments are detected and excluded), the corrected aliasing-free high resolution images (e.g., with only non-corrupted images) may be compared to an MRF dictionary (e.g., using pattern matching) to generate, for example, $T_1$, $T_2$, and ADC maps simultaneously, as described above with respect to blocks 206, 208 and 210 of FIG. 2.

As discussed above, the disclosed reconstruction method (self-calibrated subspace reconstruction) for multi-shot diffusion MRI and relaxation-diffusion quantitative MRI, may be configured to address measurement errors in images and artifacts in maps. The disclosed self-calibrated subspace reconstruction has the advantage of eliminating the need for prospective gating or extra calibration data. The disclosed self-calibrated subspace reconstruction is a data-driven subspace reconstruction that can employ joint temporally local and temporally global subspace modeling that, in some embodiments, can consist of two procedures. First, temporally local matrix completion can be employed to reconstruct aliasing-free and low-resolution images from the k-space center of the imaging data. These low resolution images may be used to identify measurement error corrupted images and generate a temporal subspace. Unlike previous methods that require extra real-time calibration data to estimate a data-driven subspace, the self-calibrated subspace reconstruction method can employ matrix completion to eliminate the need for extra calibration data. As an extension of compressed sensing, matrix completion requires low rank (or high sparsity) of data for sufficient signal recovery. The commonly used temporally global matrix completion approach, however, would fail for accurate image reconstruction, due to the weakened temporally global low-rank property (i.e., the low-rank assumption in k-t domain where t is temporally global) of data caused by the measurement errors. However, because the temporally local (shot/segment-wise) low-rank property is still satisfied, temporally local matrix completion can accurately reconstruct images where measurement errors occur randomly or locally, caused by unexpected motion or eddy currents. Second, global subspace reconstruction, where the temporal subspace is estimated from the low resolution images reconstructed using temporally local matrix completion, can be utilized to reconstruct aliasing-free and high-resolution images from the highly under-sampled k-space, including the measurement error-corrupted images. These aliasing-free high resolution images can then be used for measurement error correction to obtain, for example, artifact-free diffusion-weighted images and generate quantitative maps. The temporally global subspace reconstruction can take advantage of the data correlation across shots and segments, where images with various encodings can be acquired sequentially with shared structure and physical information. In some embodiments, the disclosed self-calibrated subspace reconstruction can be used to reconstruct mdMRF data, generating, for example, artifact-free $T_1$, $T_2$, and ADC maps simultaneously. Furthermore, the self-calibrated subspace reconstruction can be extended to other diffusion MRI techniques.

The following examples set forth, in detail, ways in which the present disclosure was evaluated and ways in which the present disclosure may be used or implemented, and will enable one of ordinary skill in the art to more readily understand the principles thereof. The following examples are presented by way of illustration and are not meant to be limiting in any way.

The example study applies the self-calibrated subspace reconstruction in mdMRF, to address measurement errors retrospectively and generate artifact-free $T_1$, $T_2$, and ADC maps without calibration data or prospective gating. The example study also investigates different options for utilizing the low-rank property, and determines the optimal scheme which can fully utilize the signal structure in mdMRF, allowing aliasing-free high-resolution image reconstruction, and high-quality quantification.

Figure 5:
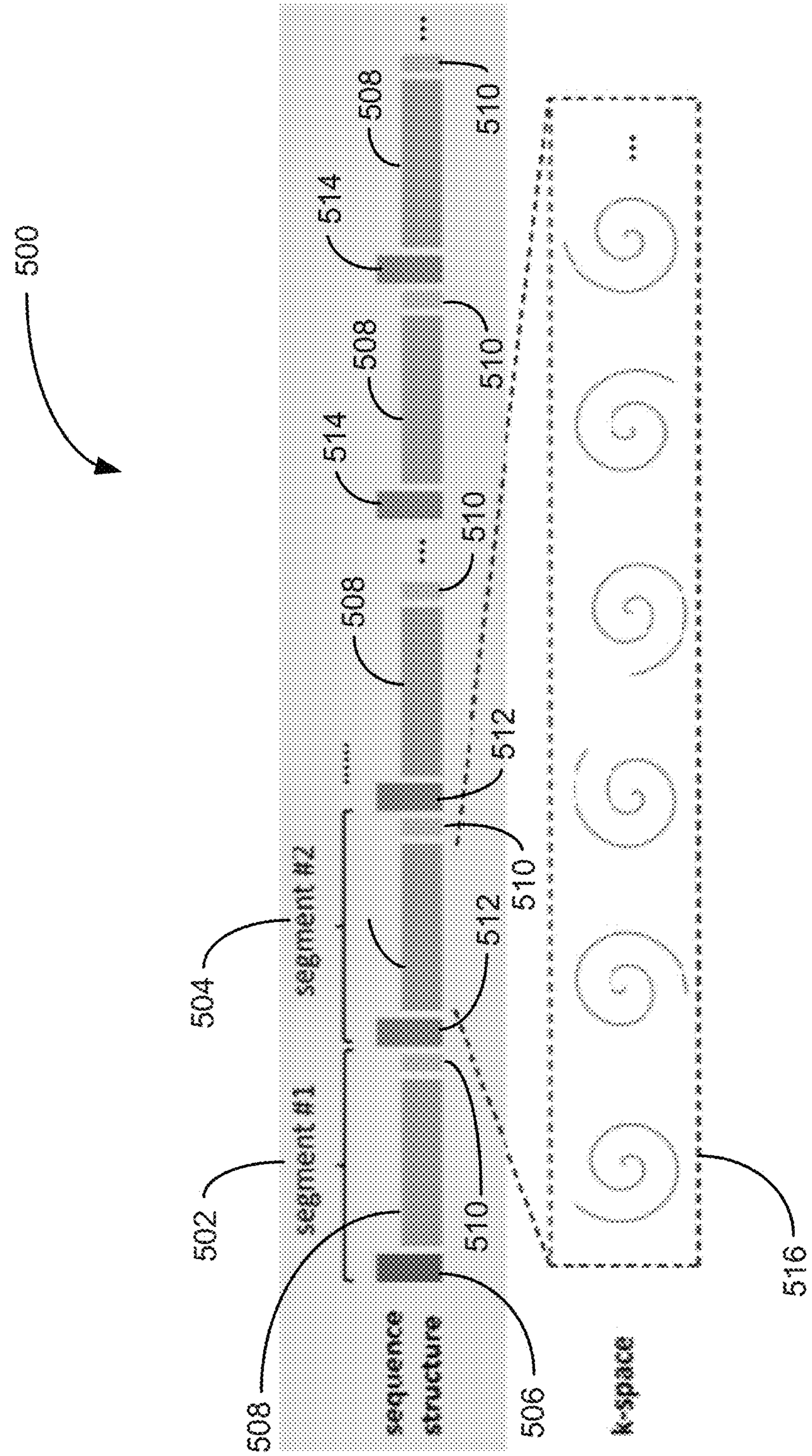
FIG. 5 shows an example pulse sequence diagram of multidimensional MRF (mdMRF) in accordance with an embodiment.

In this example study, mdMRF can be used as an example to illustrate the data acquisition and image reconstruction of multi-shot diffusion MRI and relaxation-diffusion quantitative MRI. FIG. 5 shows an example pulse sequence diagram of mdMRF in accordance with an embodiment. The example mdMRF sequence 500 consists of multiple segments, for example, first segment 502, second segment 504, and so on. Each segment can begin with a preparation module (e.g., inversion 506 for $T_1$ preparation, $T_2$ preparation 512, or diffusion preparation 514) to make the signal sensitive to relaxation and diffusion effects, followed by MRF acquisition 508, and can end with a waiting time 510 for sufficient signal recovery. The mdMRF acquisition 508 can employ a continuous and time-resolved image acquisition scheme, for example, utilizing steady-state free precession (SSFP) readouts. In some embodiments, only one k-space readout is acquired for each image to form a highly under-sampled k-space. In some embodiments, spiral trajectories with pseudo-golden-angle rotation across time points can be utilized for k-space sampling 516, creating an incoherent sampling pattern which can be crucial for the disclosed self-calibrated subspace reconstruction. As discussed above with respect to FIG. 2 (blocks 206 and 208), the self-calibrated subspace reconstruction can be performed to reconstruct a series of images from the highly under-sampled k-space 516, and pattern matching can be performed between the reconstructed images and a dictionary involving signal evolutions of different tissues generated using Bloch or extended phase graph simulation, to generate $T_1$, $T_2$, and ADC maps.

In this example study, a simulation experiment was performed to evaluate the performance of the disclosed self-calibrated subspace reconstruction method. A set of mdMRF images with 28 segments, 96 images in each segment (a total of 2688 images), where 6 segments at random locations contain measurement error-corrupted images (as shown in the reference images in FIG. 6, discussed further below) was simulated with the following parameters: FOV 300×300 $mm^2$; matrix size 192×192; resolution 1.5×1.5 $mm^2$; slice thickness 5 mm. The forward process was simulated to acquire highly under-sampled multi-channel k-space (acceleration rate=48) using Non-uniform Fast Fourier Transform (NUFFT), as well as coil sensitivity encoding using a set of coil sensitivity maps of 32 channels. White Gaussian noise, with a standard variation of 0.005 relative to the average signal magnitude for both the real and imaginary parts, can be added to the k-space data.

As mentioned above, this example study investigated different options for utilizing the low-rank property. As discussed above, the disclosed self-calibrated subspace reconstruction technique can utilize temporally local matrix completion to reconstruct or generate low resolution images from the highly under-sampled k-space. In this example, for this first procedure of the disclosed self-calibrated subspace reconstruction method (i.e., to generate low resolution images), a resolution of 3.75×3.75 $mm^2$ (2.5-fold resolution reduction) can be chosen for the low-resolution images, and $\lambda_l=5\times10^{-3}$. Two alternative techniques (i.e., temporally global matrix completion, and joint temporally local and temporally global matrix completion) for generating the low resolution images were also conducted in this example study, and compared with the temporally local matrix completion. For the temporally global matrix completion, a large rank (=40) and a small rank (=8) can respectively be used as stopping criteria. For the temporally local matrix completion, the maximum rank of 8 for all segments can be chosen as a stopping criterion. Normalized mean squared errors (NRMSEs) of the three methods (temporally local matrix completion and the two alternatives, temporally global matrix completion, and joint temporally local and temporally global matrix completion) compared to the reference were calculated in this example study. As discussed above, in the second procedure of the disclosed self-calibrated subspace reconstruction method, temporally global subspace reconstruction can be used to generate high resolution images. Two alternative techniques (i.e., temporally local subspace reconstruction, and joint temporally local and temporally global subspace reconstruction) were also conducted in this example study to reconstruct high-resolution images, and compared with the temporally global subspace reconstruction. For the sake of clear observation, the additional sparsity constraint can be eliminated (i.e., setting $\lambda=0$) for this simulation experiment. NRMSEs of the three methods (temporally global subspace reconstruction and the two alternatives, temporally local subspace reconstruction, and joint temporally local and temporally global subspace reconstruction) were calculated in this example study.

Figure 6:
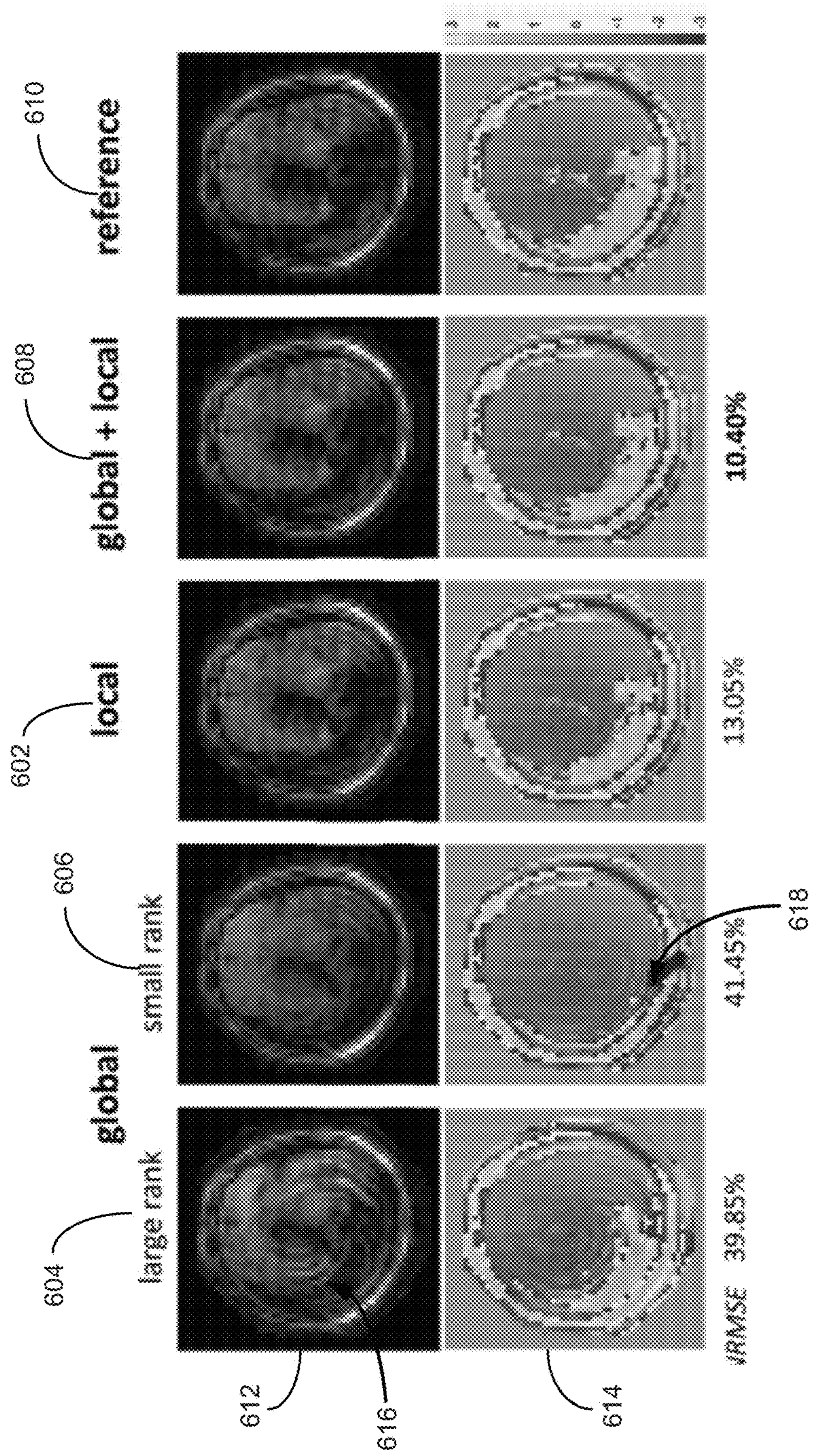
FIG. 6 illustrates an example comparison between temporally local matrix completion and two alternatives for reconstructing low-resolution images from simulated mdMRF data in accordance with an embodiment.

FIG. 6 illustrates an example comparison between temporally local matrix completion and the two alternatives, for reconstructing low-resolution images. In FIG. 6, low resolution images (resolution of 3.75×3.75 $mm^2$) are shown that, in this example study, are reconstructed from simulated mdMRF data using: 1) temporally local matrix completion 602 (third column), 2) temporally global matrix completion 604, 606 (first and second column), and 3) joint temporally local and temporally global matrix completion 608 (fourth column). Magnitude images 612 (top row) and phase images 614 (bottom row) are shown. Arrow 616 points out severe aliasing artifacts, and the arrow 618 points out the missing phase information. Reference images 610 are shown in the 5th column. As shown in FIG. 6, temporally global low-rank matrix completion 604, 606 fails to accurately reconstruct the low-resolution images (1st and 2nd columns). Specifically, when a large rank 604 (=40) is chosen as a stopping criterion, the aliasing artifacts are still severe (as pointed out by arrow 616). In contrast, when a small rank 606 (=8) is chosen, the signal components corresponding to small singular values (e.g., the phase variation, as pointed out by arrow 618) are not recovered. The temporally local low-rank matrix completion 602 can significantly reduce the aliasing artifact, and accurately recover the phase variation meanwhile (3rd column). Joint temporally local and temporally global matrix completion 608 (4th column) has a very slight improvement compared to the temporally local matrix completion 602 in terms of NRMSEs. Therefore, temporally local matrix completion can advantageously be chosen for the first procedure or step of the disclosed self-calibrated subspace reconstruction to generate low-resolution images that can be used as calibration data.

Figure 7:
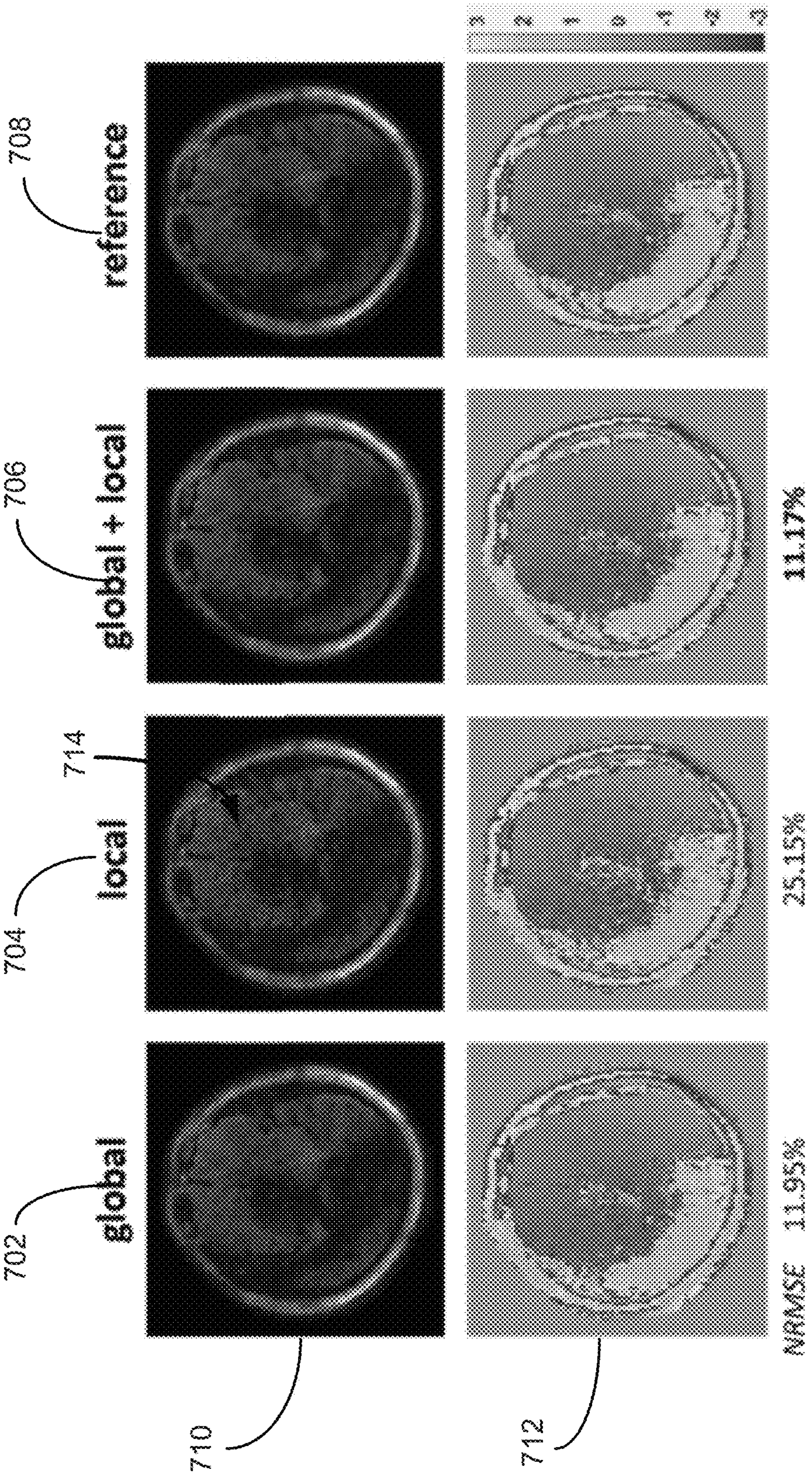
FIG. 7 illustrates an example comparison between temporally global subspace reconstruction and two alternatives for reconstructing high-resolution images in accordance with an embodiment.

FIG. 7 illustrates an example comparison between temporally global subspace reconstruction and two alternatives for reconstructing high-resolution images. In FIG. 7, high resolution images (resolution of 1.5×1.5 $mm^2$) are shown that, in this example study, are reconstructed using: 1) temporally global subspace reconstruction 702 (first column), 2) temporally local subspace reconstruction 704 (second column), and 3) joint temporally local and temporally global subspace reconstruction 706 (third column). Magnitude images 710 (top row) and phase images 712 (bottom row) are shown. Arrow 714 points out the severe noise in the reconstructed images. Reference images 708 are shown in the 4th column. As shown in FIG. 7, all the methods (i . . . , temporally global subspace reconstruction 702, temporally local subspace reconstruction 704, and joint temporally local and temporally global subspace reconstruction 706) can reconstruct aliasing-free high-resolution images. However, the signal-to-noise ratio (SNR) is very low in the reconstructed images using temporally local subspace reconstruction 704 (2nd column, as pointed out by arrow 714). The temporally global subspace reconstruction 702 can reconstruct images with much-improved SNR than those using temporally local subspace reconstruction 704. Joint temporally local and temporally global subspace reconstruction 706 (3rd column) has a very slight improvement compared to temporally global subspace reconstruction 702 in terms of NRMSEs. Temporally global subspace reconstruction 702 can advantageously be chosen for reconstructing the high resolution images in the second step or procedure of the disclosed self-calibrated subspace reconstruction method because the difference is slight and the subsequent dictionary matching (e.g., as discussed above with respect to FIGS. 2 and 3) can further correct for incoherent artifacts.

In this example study, the disclosed self-calibrated subspace reconstruction was applied to reconstruct mdMRF data, to address the measurement errors retrospectively, and to generate artifact-free $T_1$, $T_2$, and ADC maps. The measurement errors usually occur in mdMRF scans without peripheral pulsation gating, because cardiac pulsation is a major source of such measurement errors. However, sometimes there can also be measurement errors in the mdMRF scan with peripheral pulsation gating because of other factors or failed gating. The disclosed self-calibrated subspace reconstruction technique can address this issue for both types of scans (i.e., with and without peripheral pulsation gating). In this example study, the process for mdMRF quantification using the disclosed self-calibrated subspace reconstruction can be as follows: 1) Obtain (or generate) aliasing-free and high-resolution images, including the corrupted and non-corrupted images, using the disclosed self-calibrated subspace reconstruction method; 2) Detect and correct (exclude) the corrupted images using a customized outlier detection algorithm; 3) Generate artifact-free T1, T2, and ADC maps using pattern matching for the high-resolution images after correction (e.g., with only non-corrupted images).

In this example study, a discussed above, a sequence structure such as shown in FIG. 5 can be used for the mdMRF scan. Linear encoding (LTE) can be used for diffusion preparation 514 (shown in FIG. 5) and steady-state free precession (SSFP) can be used for MRF readouts 508 (shown in FIG. 5) in this example study. Five healthy volunteers (Subjects 1-5) were used and one volunteer (Subject 1) was scanned for a feasibility evaluation experiment and a scan efficiency investigation experiment. The other four volunteers (Subjects 2-5) were scanned for a robustness evaluation experiment among different subjects and under variant imaging settings (e.g., scanners and b-value combinations for diffusion encoding).

In the feasibility evaluation experiment and the scan efficiency investigation experiment of this example study, Subject 1 was scanned on a 3T scanner equipped with a 32-channel head coil. Two mdMRF scans were performed (one with and the other without peripheral pulsation gating), with the following parameters: TI (21 ms) for $T_1$ preparation; TE (30, 50, 65 ms) for $T_2$ preparation; b-values (300, 700, $1000\times10^{-6}$ s/mm$^2$) with three encoding directions for diffusion preparation; SSFP with constant flip angles of 10 degrees for MRF readouts; FOV 300×300 mm$^2$; resolution 1.5×1.5 mm$^2$; slice thickness 5 mm. In the feasibility evaluation experiment, 28 acquisition segments, each with 96 images, were acquired. The scan time was 26 s for both non-gated and gated scans. In this example study, a conventional MRF scan was performed for $T_1$ and $T_2$ references, and an EPI-based diffusion scan was also acquired for ADC reference.

In the scan efficiency investigation experiment of this example study, Subject 1 was scanned with several slices and at different dates to provide 7 cases. Here, one case means a scan at a different slice or date. In each case, 64 segments were acquired, and a series of segments were truncated for reconstruction to investigate the minimum number of segments and scan time needed for good-quality T1, T2, and ADC mapping.

In the robustness evaluation experiment of this example study, two subjects (Subjects 2 and 3) were scanned on the 3T scanner described above, and the other two (Subjects 4 and 5) were scanned on a 3T scanner equipped with a 44-channel head coil. Only mdMRF scans without pulsation gating were performed, with different b-value combinations: 300, 700, $1000\times10^{-6}$ s/mm$^2$ (Subjects 2 and 4); 100, 400, $800\times10^{-6}$ s/mm$^2$ (subject 3); 700, $1000\times10^{-6}$ s/mm$^2$ (Subject 5). Other imaging parameters were the same as in the feasibility evaluation experiment.

In this example study, all the mdMRF data were reconstructed using the proposed self-calibrated subspace reconstruction. The regularization parameter $\lambda_l=5\times10^{-3}$ was used in the first procedure to generate the low resolution images, and $\lambda=4\times10^{-3}$ was used in the second procedure to generate the high resolution images. In this example study, it took about 1 hour (first procedure: ~50 minutes; second procedure: ~10 minutes) for the reconstruction of each mdMRF data.

As discussed above with respect to FIG. 3, the reconstructed high resolution images may be processed to detect and correct measurement errors. For example, in this example study a detection algorithm (e.g., a customized outlier detection algorithm as described above with respect to FIG. 4) can be used to detect corrupted segments (or images) and a correction strategy can be used that includes directly excluding the detected corrupted segments.

After removing the corrupted images, the following example parameter mapping step was used in this example study to generate $T_1$, $T_2$, and ADC maps. A dictionary can be simulated using known methods for mdMRF quantification techniques. In this parameter mapping step of the example study, the dictionary can also be corrected by excluding the segments corresponding to the corrupted segments of reconstructed images. Pattern matching was then performed between the corrected dictionary and the corrected images to generate $T_1$, $T_2$, $M_0$, and ADC maps simultaneously.

In the feasibility evaluation experiment of this example study, six brain regions of interest (ROIs), i.e., frontal white matter (WM-Frontal), putamen grey matter (GM-Putamen), and parietal white matter (WM-Parietal), each with both left and right sides, were chosen for quantitative analysis. The average $T_1$, $T_2$, and ADC values in each ROI were calculated. The comparison was performed between the mdMRF scans with and without peripheral pulsation gating, before and after correction, as well as the reference.

Figure 8:
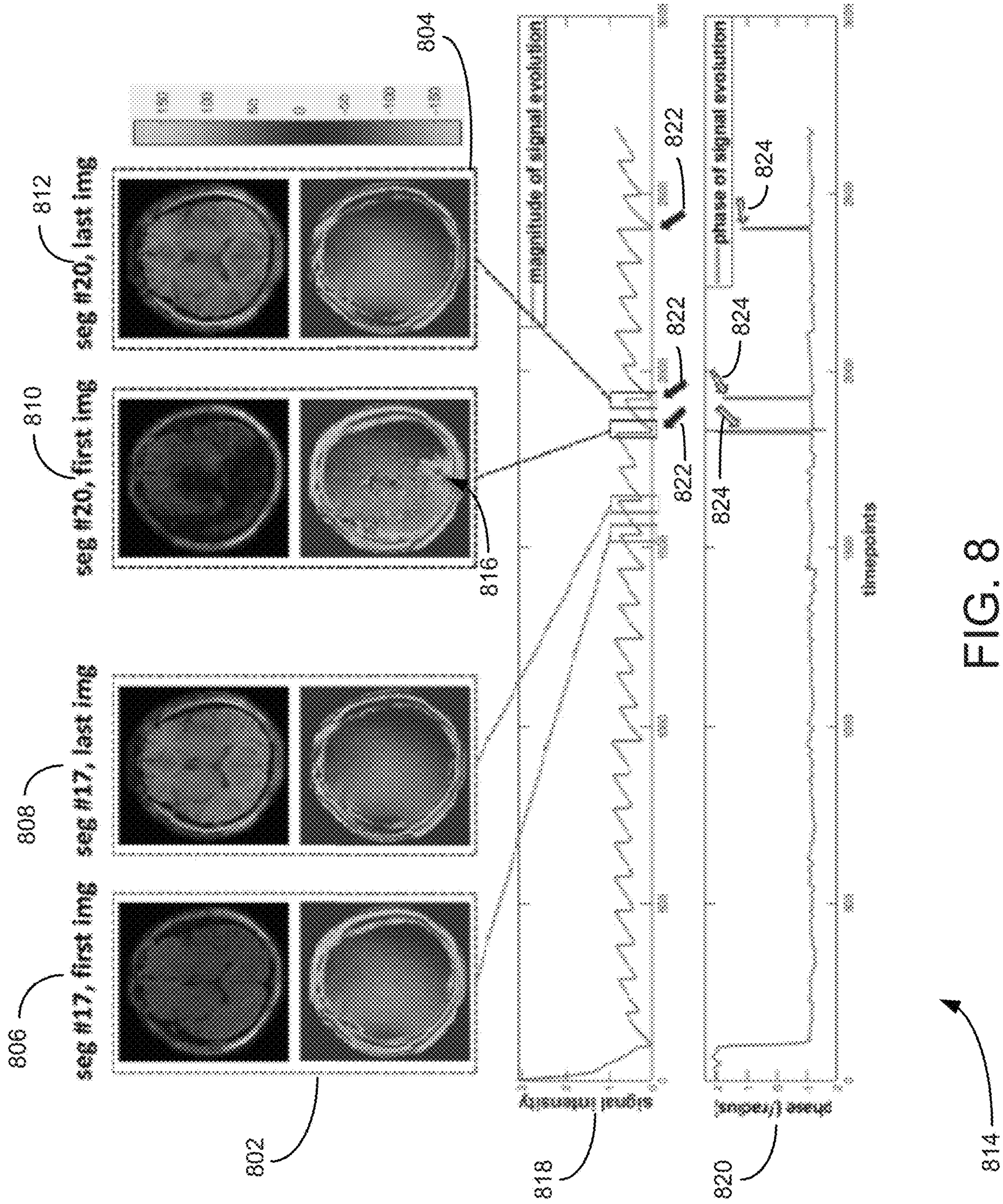
FIG. 8 illustrates 1) image artifacts caused by measurement errors at three places in the diffusion-prepared segments of an mdMRF scan without peripheral pulsation gating, and 2) an example signal evolution curve corresponding to a voxel in accordance with an embodiment.

With regard to the feasibility evaluation experiment of this example study, FIG. 8 illustrates 1) image artifacts caused by measurement errors at three places in the diffusion-prepared segments of an mdMRF scan without peripheral pulsation gating, and 2) an example signal evolution curve corresponding to a voxel in accordance with an embodiment. The images shown in FIG. 8 have been reconstructed using the disclosed self-calibrated subspace reconstruction and correspond to four representative time points, namely, the first image 806 and the last image 808 of a non-corrupted segment 802 and the first image 810 and the last image 812 of a corrupted segment 804. In each corrupted segment, the first few images can be corrupted by measurement errors (i.e., inter- and intra-segment magnitude and phase variations) and the measurement errors can become smaller gradually and quickly, and finally disappear in the last few images. In FIG. 8, the first 810 and last 812 images of the 20th segment are shown for an example of a corrupted segment 804. In contrast, in each non-corrupted segment, there are no measurement errors. In FIG. 8, the first 806 and last 808 images of the 17th segment are shown for an example of a non-corrupted segment 802. Note that the magnitude variation in this example means magnitude attenuation or signal void, but not signal recovery or decay. These measurement errors can also be viewed in a signal evolution curve 814. FIG. 8 shows an example signal evolution curve 814 corresponding to a voxel (as pointed out by arrow 816 in the 3rd column of images in FIG. 8). The signal evolution curve include a magnitude 818 and phase 820 component. The magnitude variation appears as magnitude attenuation or signal void, and the phase variation appears as fluctuation at the start of each corrupted segment. They occur at random locations and, in this example, only a few segments were corrupted. In FIG. 8, the arrows 822 point out the magnitude variations and arrows 824 point out the phase variations in the corrupted segments.

Figure 9:
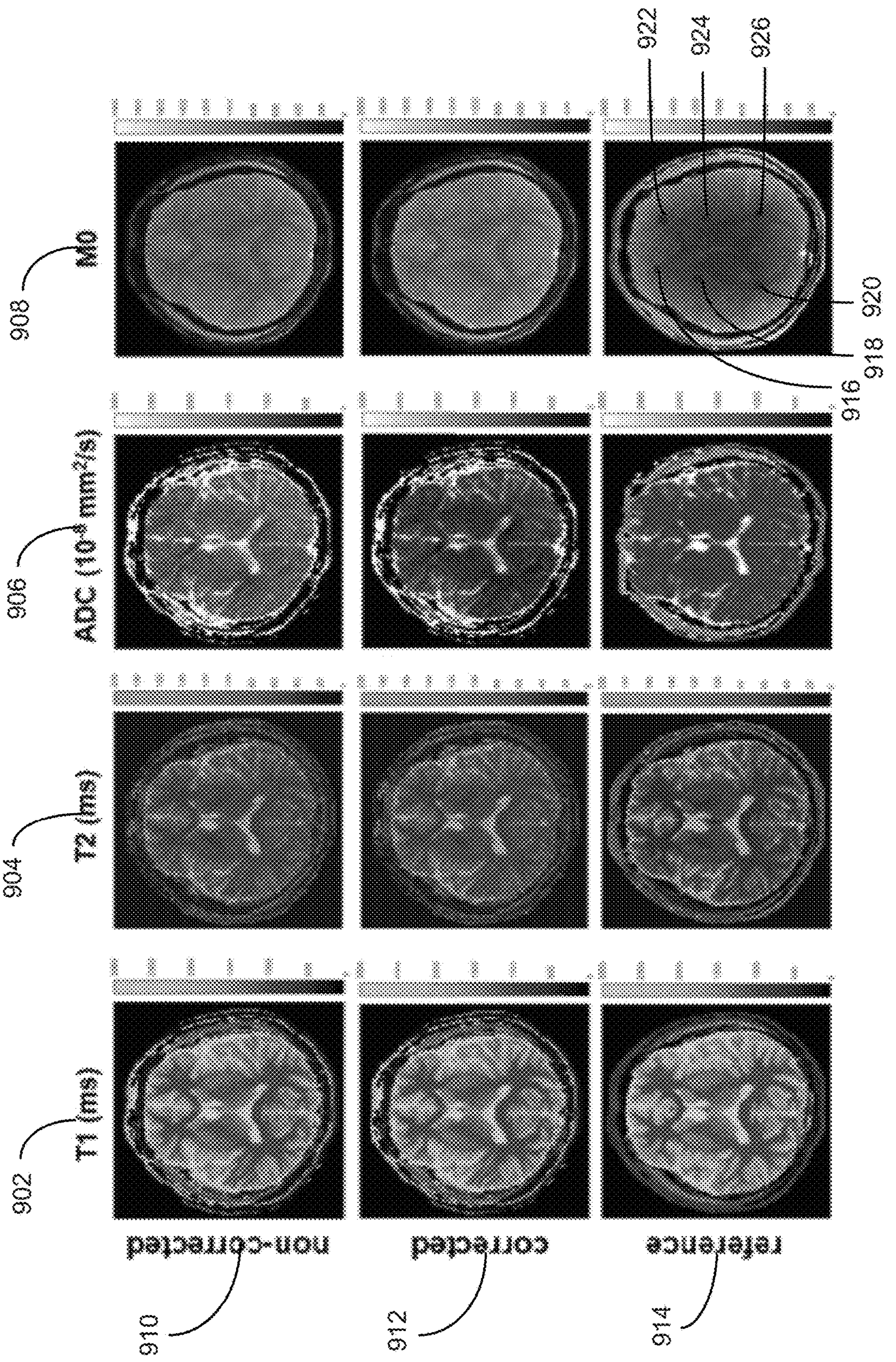
FIG. 9 shows example $T_1$, $T_2$, and ADC maps generated from an mdMRF scan without peripheral pulsation gating and using self-calibrated subspace reconstruction in accordance with an embodiment.

FIG. 9 shows example $T_1$, $T_2$, and ADC maps generated from an mdMRF scan without peripheral pulsation gating and using the disclosed self-calibrated subspace reconstruction in accordance with an embodiment. In FIG. 9, the first column 902 shows $T_1$ maps, the second column 904 shows $T_2$ maps, the third column 906 shows ADC maps and the fourth column 908 shows $M_o$ maps. The top row 910 includes maps generated before correction of the reconstructed images, the middle row 912 includes maps generated after correction of the reconstructed images, and the bottom row 914 includes reference maps. Before the correction of the reconstructed images, there are severe shading artifacts, which appear as uneven and overestimated ADC values, in the ADC map (third column 906, top row 910). After the correction of the reconstructed images, the shading artifacts are addressed and the accuracy of the ADC map is significantly improved (third column 906, middle row 912) and closer to the reference (third column 906, bottom row 914). $T_1$ and $T_2$ maps (first 902 and second 904 columns, respectively) are unaffected and consistent before and after correction (top 910 and middle 921 rows, respectively). The $T_2$ values in $T_2$ maps generated by mdMRF are a little higher than those in the reference. In FIG. 9, six regions of interest (ROIs) 918, 920, 922, 924, 926, 928 for quantitative analysis are overlayed on the $M_0$ map of the reference (fourth column 908, bottom row 914).

Figure 10:
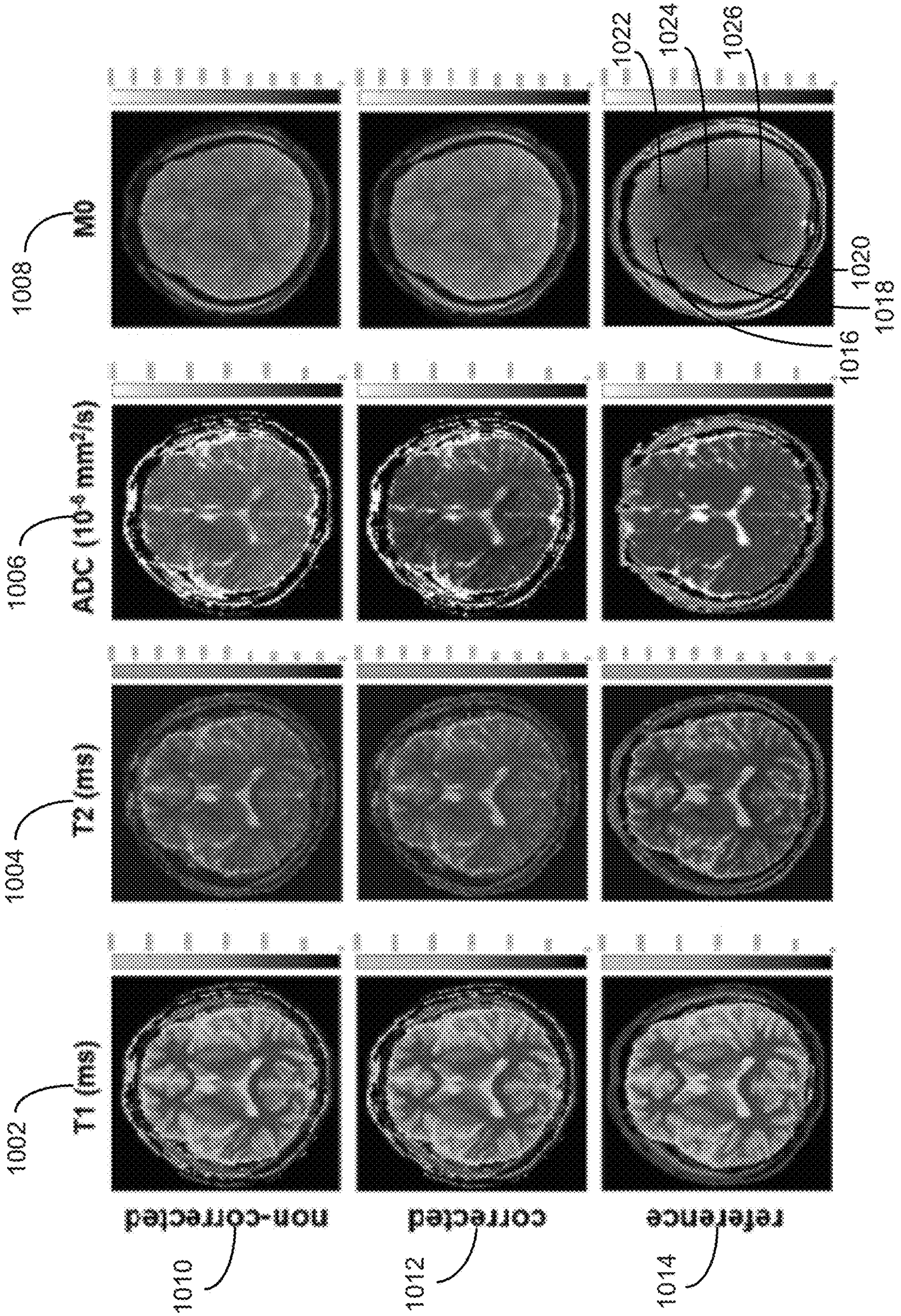
FIG. 10 shows example $T_1$, $T_2$, and ADC maps generated from an mdMRF scan with prospective peripheral pulsation gating and using self-calibrated subspace reconstruction in accordance with an embodiment.

FIG. 10 shows example $T_1$, $T_2$, and ADC maps generated from an mdMRF scan with prospective peripheral pulsation gating and using the disclosed self-calibrated subspace reconstruction in accordance with an embodiment. In FIG. 10, the first column 1002 shows $T_1$ maps, the second column 1004 shows $T_2$ maps, the third column 1006 shows ADC maps and the fourth column 1008 shows $M_o$ maps. The top row 1010 includes maps generated before correction of the reconstructed images, the middle row 1012 includes maps generated after correction of the reconstructed images, and the bottom row 1014 includes reference maps. Although gating was used to avoid the impact of cardiac pulsation on diffusion encoding segments, in this example, there are still severe shading artifacts in the ADC map before correction (third column 1006, top row 1010) of the reconstructed images because of failed peripheral pulsation gating. After correction of the reconstructed images, the shading artifacts are addressed and the ADC map (third column 1006, middle row 1012) is closer to the reference (third column 1006, bottom row 1014). In FIG. 10, six ROIs 1016, 1018, 1020, 1022, 1024, 1026 for quantitative analysis are overlayed on the $M_0$ map of the reference (fourth column 1008, bottom row 1014).

In this example study, quantitative analysis of the six brain ROIs (shown in FIGS. 9 and 10) illustrated that the average $T_1$ and $T_2$ values for the six ROIs were highly consistent before and after correction, for both mdMRF scans with and without gating. In the non-corrected cases (both with and without gating) the ADC values were significantly biased (overestimated), while in the corrected cases the ADC values were more accurate compared to the reference. The average $T_2$ values generated by mdMRF scans were a little (~10 ms) higher than the reference.

Figure 11:
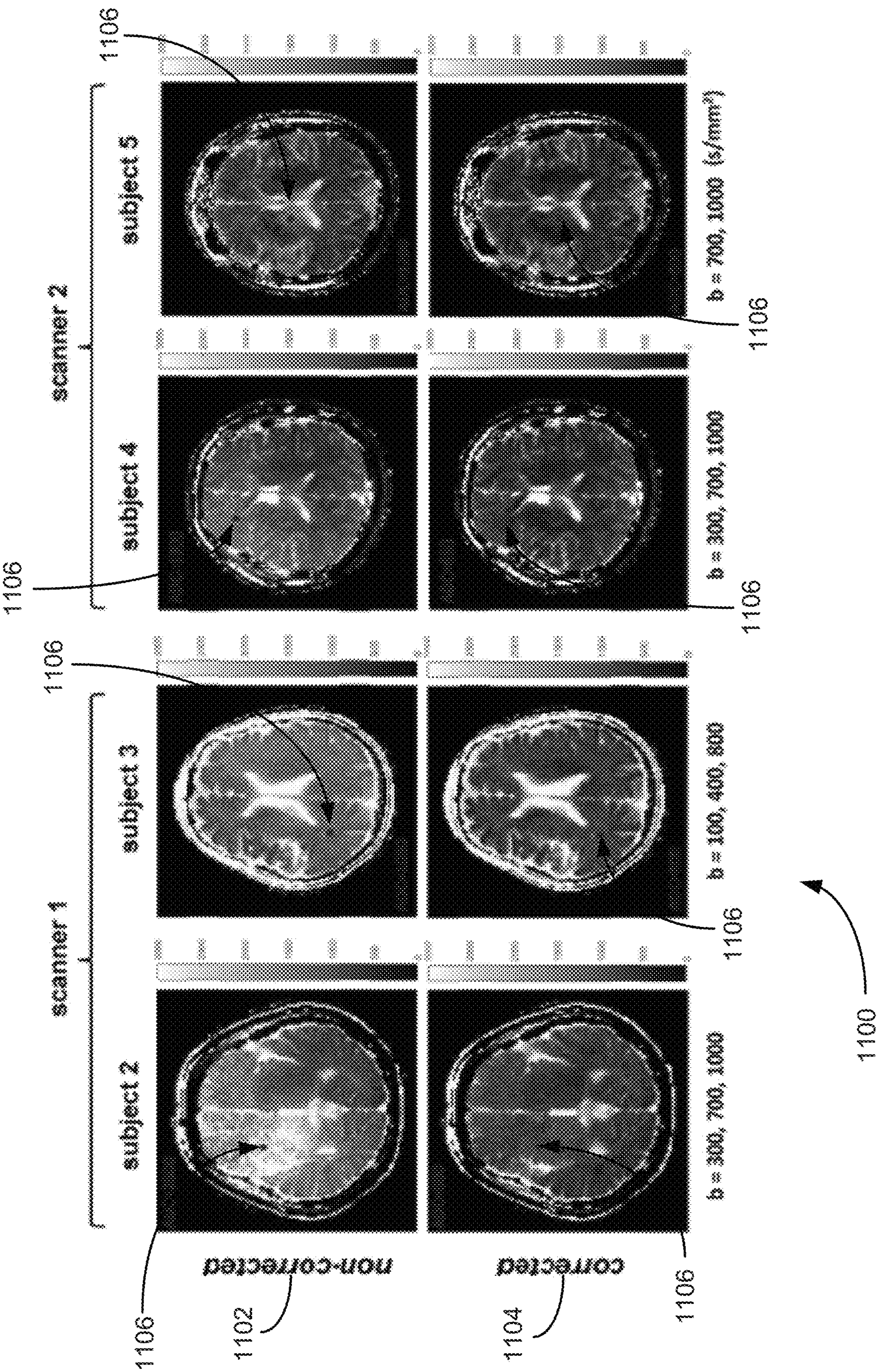
FIG. 11 shows example ADC maps generated from mdMRF scans without peripheral pulsation gating and using self-calibrated subspace reconstruction in accordance with an embodiment.

With regard to the robustness evaluation experiment of this example study, FIG. 11 shows example ADC maps 1100 generated from mdMRF scans without peripheral pulsation gating, and using the disclosed self-calibrated subspace reconstruction, among different subjects and under variant imaging settings (e.g., different scanners and b-values for diffusion encoding). In FIG. 11, the top row 1102 includes maps generated before correction of the reconstructed images, and the bottom row 1104 includes maps generated after correction of the reconstructed images. In each ADC map, arrows 1106 indicate a location with shading artifacts, and the number beside shows the corresponding ADC value. In each case (subjects 2, 3, 4 and 5), there are severe shading artifacts in the ADC map before correction (top row 1102) and the number shown beside indicates an overestimated ADC value. These shading artifacts appear at different locations in different cases, indicating that measurement errors occur randomly. The shading artifact was addressed after correction (bottom row 1104), with a much more reasonable ADC map and values.

Figure 12:
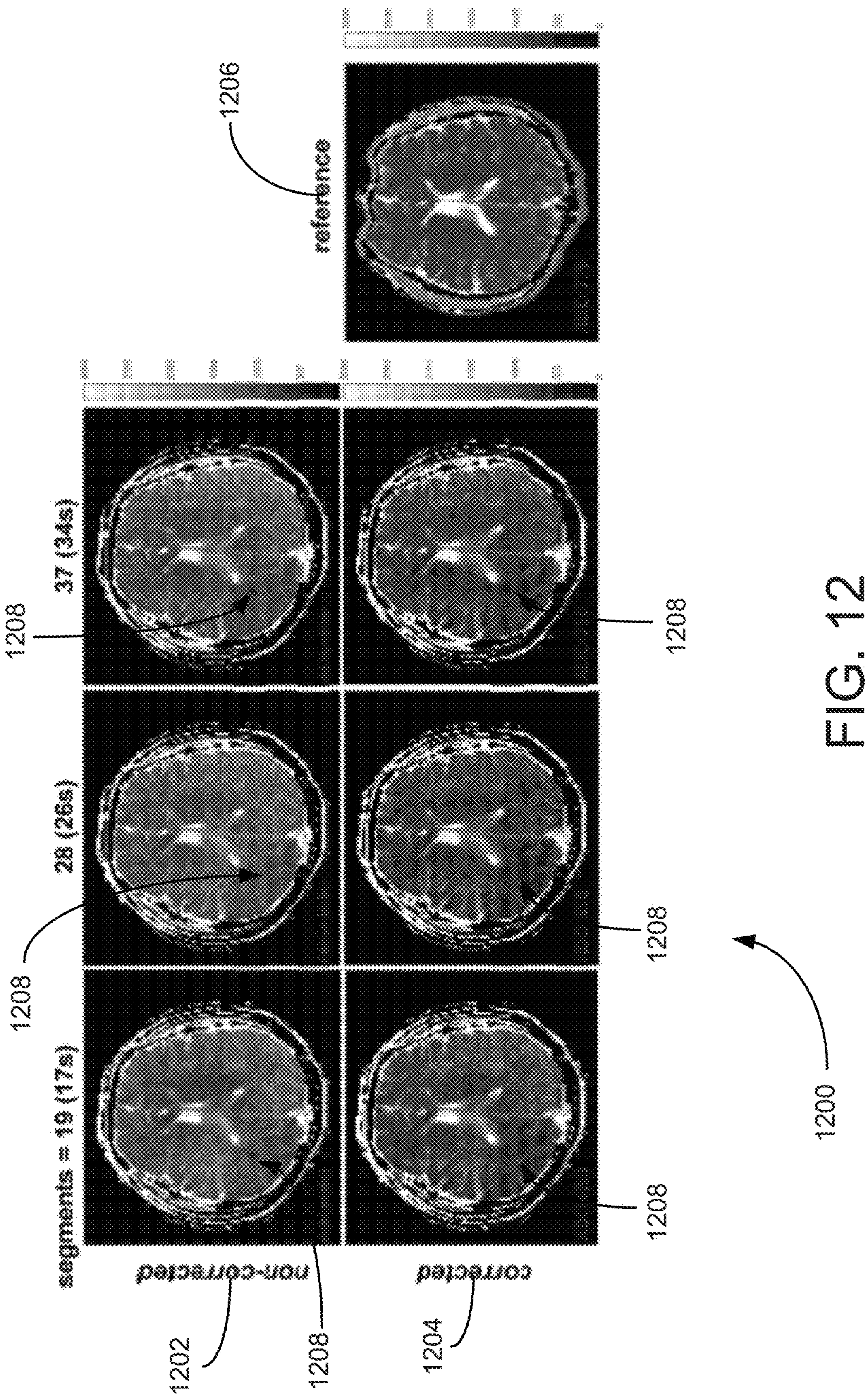
FIG. 12 shows example ADC maps generated from an mdMRF scan without peripheral pulsation gating and using self-calibrated subspace reconstruction in accordance with an embodiment.

This example study also performed a scan efficiency investigation experiment. FIG. 12 shows example ADC maps 1200 generated from an mdMRF scan without peripheral pulsation gating, and using the disclosed self-calibrated subspace reconstruction, with the use of a different total number of the segment (19, 28, and 37), which is corresponding to different scan times (17, 26, and 34 seconds). In FIG. 12, the top row 1202 includes maps generated before correction of the reconstructed images, and the bottom row 1204 includes maps generated after correction of the reconstructed images. FIG. 12 also shows a reference map 1206. In each ADC map, arrows 1206 indicate representative locations, and the number beside shows the corresponding ADC value. There can be a tradeoff between robustness and scan efficiency. More segments lead to better ADC maps (i.e., the ADC values are closer to the reference), but need more scan time. In this example study, seven cases were tested and counted. In principle, the correction (exclusion) of corrupted segments can lead to a reduction in scan efficiency. However, an average scan time of <20 seconds per slice can be achieved because only a few segments were corrupted and needed to be excluded.

As mentioned, the disclosed self-calibrated subspace reconstruction method can be used to address the artifacts caused by measurement errors (i.e., inter- and intra-segment magnitude and phase variations) retrospectively in diffusion MRI. These measurement errors can be caused by physiological motion (e.g., cardiac pulsation), bulk motion, and eddy currents during diffusion encoding. The disclosed reconstruction method can be a time-resolved reconstruction, where images are reconstructed for each time point (or readout), but without the need for extra calibration data. To overcome the challenge that the commonly used temporally global matrix completion is not applicable because the temporally global low-rank property is weakened by measurement errors, joint temporally local and temporally global subspace modeling can be used in the self-calibrated subspace reconstruction. Specifically, in some embodiments the self-calibrated subspace reconstruction can implemented in a two-step manner: 1) generate (or obtain) aliasing-free and low-resolution images from the central k-space of imaging data using temporally local matrix completion; and 2) generate (or obtain) aliasing-free and high-resolution images from the highly under-sampled imaging data using temporally global subspace reconstruction, where the temporal subspace is estimated from the low-resolution images. Furthermore, joint temporally local and temporally global subspace modeling has several additional advantages. First, smaller size (low-resolution) data can be used to reduce the computation burden of matrix completion in the first procedure (or step), while the large size (high-resolution) data is only reconstructed in the second procedure (or step) using subspace reconstruction which is much more computation- and memory-saving than matrix completion. This strategy can reduce time by about 3-fold compared to reconstruction using temporally local matrix completion for high-resolution data. Second, the proposed self-calibrated subspace reconstruction method can take advantage of the feature of non-Cartesian sampling, i.e., the central k-space is typically more densely sampled (or with lower acceleration), which is beneficial for image reconstruction using matrix completion. The temporally local matrix completion can explore the local low-rank prior in the temporal dimension according to the signal structure of the data.

In some embodiments, the self-calibrated subspace reconstruction can be applied to mdMRF. Aliasing-free and high-resolution images, including non-corrupted and corrupted images, can be reconstructed. This is achievable because the data-driven subspace can capture both the signal and measurement errors. In contrast, dictionary-based subspace reconstruction as used in prior mdMRF techniques is not able to provide accurate reconstruction for data contaminated by measurement errors, because the measurement errors are not accounted for in signal modeling (i.e., dictionary generation) and would result in artifacts in, for example, an ADC map. In some embodiments, paired with a customized outlier detection algorithm, the corrupted segments can be automatically detected and corrected. Because aliasing-free and high-resolution images can be obtained using the disclosed self-calibrated subspace reconstruction, automatic and robust detection of the corrupted segments is achievable. Because the measurement errors involve both magnitude and phase variations, in some embodiments the exclusion of the corrupted segments can be adopted as the correction strategy, unlike the phase correction commonly used in other diffusion MRI techniques. In principle, this correction strategy can reduce the scan efficiency. However, because mdMRF employs randomized waiting times, which imposes incoherence between the timings of diffusion encoding and motions, only a few segments would be corrupted and need to be excluded. This strategy can avoid the worst case that all physiological motion (e.g., cardiac pulsation) is aligned with diffusion preparations, making most of the diffusion-weighted segments corrupted. In some embodiments, a scan time of <20 seconds per slice can still be achieved. In some embodiments, the distribution of preparation modules can also be optimized (or randomized) to further improve the incoherence between diffusion encoding and motions.

The disclosed self-calibrated subspace reconstruction method can allow for the peripheral pulsation gating in mdMRF to be dropped off, to overcome the limitations with gating. In some cases of mdMRF with peripheral pulsation gating, there are still severe measurement errors and shading artifacts because of failed triggers. For these cases, the disclosed self-calibrated subspace reconstruction can also be used to address measurement errors and shading artifacts. This indicates that the disclosed self-calibrated subspace reconstruction method can provide more robust mapping compared to using peripheral pulsation gating.

In some embodiments, the time required for performing the disclosed self-calibrated subspace reconstruction can be improved by using a GPU-based NUFFT implementation. In addition, in some embodiments spiral trajectories with denser central k-space sampling can further improve the condition for matrix completion and thus reduce the iterations of matrix completion. In some embodiments, a sliding window size of 5 can be used and is small enough in mdMRF for accurate $T_1$, $T_2$, and ADC mapping. In some embodiments, other physical and image priors, e.g., sparsity in spatial and temporal dimension, locally low rank, structured low rank, and patch-based low rank, could be additionally combined for further improvement of image reconstruction.

As mentioned above, in some embodiments, the disclosed self-calibrated subspace reconstruction method can be a data-driven subspace reconstruction method using joint temporally local and temporally global subspace modeling to reconstruct time-resolved images. In the example study described above, the disclosed self-calibrated subspace reconstruction was applied in mdMRF. However, in some embodiments the disclosed self-calibrated subspace reconstruction can be extended to other diffusion MRI techniques that adopt time-resolved image acquisition and reconstruction, e.g., MR Multitasking. Additionally, in some embodiments the disclosed self-calibrated subspace reconstruction can also be applied to other dynamic imaging techniques, where exploring data correlation across time points is crucial to reconstruct aliasing-free images with a high temporal resolution, e.g., abdominal imaging, especially to correct irregular motion.

Figure 13:
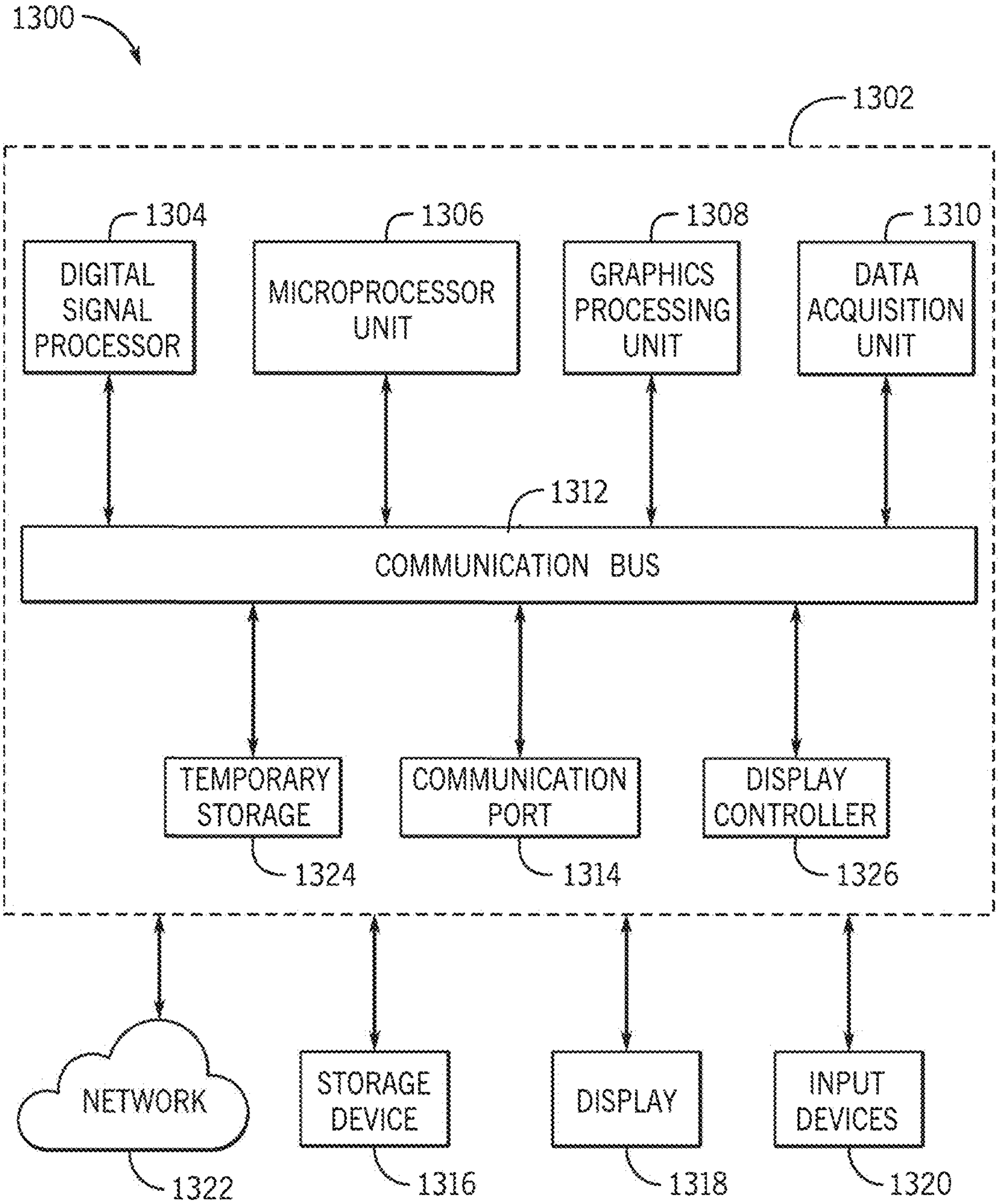
FIG. 13 is a block diagram of an example computer system in accordance with an embodiment.

FIG. 13 is a block diagram of an example computer system in accordance with an embodiment. Computer system 1300 may be used to implement the systems and methods described herein. In some embodiments, the computer system 1300 may be a workstation, a notebook computer, a tablet device, a mobile device, a multimedia device, a network server, a mainframe, one or more controllers, one or more microcontrollers, or any other general-purpose or application-specific computing device. The computer system 1300 may operate autonomously or semi-autonomously, or may read executable software instructions from the memory or storage device 1316 or a non-transitory computer-readable medium (e.g., a hard drive, a CD-ROM, flash memory), or may receive instructions via the input device 1320 from a user, or any other source logically connected to a computer or device, such as another networked computer or server. Thus, in some embodiments, the computer system 1300 can also include any suitable device for reading computer-readable storage media.

Data, such as data acquired with, for example, an imaging system (e.g., a magnetic resonance imaging (MRI) system, etc.), may be provided to the computer system 1300 from a data storage device 1316, and these data are received in a processing unit 1302. In some embodiments, the processing unit 1302 included one or more processors. For example, the processing unit 1302 may include one or more of a digital signal processor (DSP) 1304, a microprocessor unit (MPU) 1306, and a graphic processing unit (GPU) 1308. The processing unit 1302 also includes a data acquisition unit 1310 that is configured to electronically receive data to be processed. The DSP 1304, MPU 1306, GPU 1308, and data acquisition unit 1310 are all coupled to a communication bus 1312. The communication bus 1312 may be, for example, a group of wires, or a hardware used for switching data between the peripherals or between any component in the processing unit 1302.

The processing unit 1302 may also include a communication port 1314 in electronic communication with other devices, which may include a storage device 1316, a display 1318, and one or more input devices 1320. Examples of an input device 1320 include, but are not limited to, a keyboard, a mouse, and a touch screen through which a user can provide an input. The storage device 1316 may be configured to store data, which may include data such as, for example, MR or MRF data of a subject, aliasing-free low resolution images, estimated temporally global subspace, aliasing-free high resolution images, corrected aliasing-free high resolution images, quantitative parameters, parameter maps etc., whether these data are provided to, or processed by, the processing unit 1302. The display 1318 may be used to display images, reports, and other information, such as patient health data, and so on.

The processing unit 1302 can also be in electronic communication with a network 1322 to transmit and receive data and other information. The communication port 1314 can also be coupled to the processing unit 1302 through a switched central resource, for example the communication bus 1312. The processing unit 1302 can also include temporary storage 1324 and a display controller 1326. The temporary storage 1324 is configured to store temporary information. For example, the temporary storage 1324 can be a random-access memory.

Computer-executable instructions for reconstructing MR or MRF images using a self-calibrated subspace reconstruction according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for reconstructing time-resolved images using a self-calibrated subspace reconstruction, the method comprising:

- receiving data acquired from a subject using a magnetic resonance imaging (MRI) system;
- generating aliasing-free low resolution images from at least a portion of the received data using temporally local low-rank matrix completion;
- estimating a temporally global subspace using the aliasing-free low resolution images; and
- generating aliasing-free high resolution time-resolved images from the received data using temporally global subspace reconstruction that utilizes the estimated temporally global subspace.

2. A magnetic resonance imaging (MRI) system comprising:

- a magnet system configured to generate a polarizing magnetic field about a portion of a subject positioned;
- a magnetic gradient system including a plurality of magnetic gradient coils configured to apply at least one magnetic gradient field to the polarizing magnetic field;
- a radio frequency (RF) system configured to apply an RF excitation field to the subject, and to receive magnetic resonance signals from the subject using a coil array; and
- at least one processor configured to:
  - direct the plurality of magnetic gradient coils and the RF system to perform a pulse sequence to acquire data from a subject;
  - generate aliasing-free low resolution images from at least a portion of the received data using temporally local low-rank matrix completion;
  - estimate a temporally global subspace using the aliasing-free low resolution images; and
  - generate aliasing-free high resolution time-resolved images from the received data using temporally global subspace reconstruction that utilizes the estimated temporally global subspace.

3. A non-transitory, computer readable medium storing instructions that, when executed by one or more processors, perform a set of functions, the set of functions comprising:

- receiving data acquired from a subject using a magnetic resonance imaging (MRI) system;
- generating aliasing-free low resolution images from at least a portion of the received data using temporally local low-rank matrix completion;
- estimating a temporally global subspace using the aliasing-free low resolution images; and
- generating aliasing-free high resolution time-resolved images from the received data using temporally global subspace reconstruction that utilizes the estimated temporally global subspace.

4. The method according to claim 1, further comprising generating a set of corrected high resolution images from the aliasing-free high resolution time-resolved images.

5. The method according to claim 1, wherein the received data is magnetic resonance fingerprinting (MRF) data, and wherein the aliasing-free high resolution time-resolved images are magnetic resonance fingerprinting (MRF) images.

6. The method according to claim 1, wherein the received data is multidimensional magnetic resonance fingerprinting (mdMRF) data, and wherein the aliasing-free high resolution time-resolved images are multidimensional magnetic resonance fingerprinting (mdMRF) images.

7. The method according to claim 1, wherein the at least a portion of the received data is a set of central k-space data extracted from the received data.

8. The method according to claim 1, wherein the temporally local low-rank matrix completion comprises a model given by:

$$\hat{m}_c = \underset{m_c}{\operatorname{argmin}} \left\|\hat{d}_c - \Omega F S_c m_c\right\|_2^2 + \lambda_l \sum_{s=1}^{N_s} \|m_{c,s}\|_*$$

where $\hat{d}_c$ is a set of central k-space extracted from the received data, $S_c$ is the low-resolution coil sensitivity estimated from fully sampled data by combining $\hat{d}_c$ along the time dimension, F and Ω denote the Fourier encoding in the spatial domain and under-sampling mask in k-t domain, respectively, $m_c$ is the low-resolution image series (x-t domain) to be reconstructed, and $m_{c,s}$ is a portion of $m_c$ corresponding to s-th segment, $N_s$ is the number of segments and $\lambda_l$ is the regularization parameter.

9. The method according to claim 1, wherein estimating the temporally global subspace using the aliasing-free low resolution images comprises performing singular value decomposition and truncation on the aliasing-free low resolution images.

10. The method according to claim 1, wherein the temporally global subspace reconstruction comprises a model given by:

$$\hat{U} = \underset{U}{\operatorname{argmin}} \left\|d_u - \Omega F S U V^H\right\|_2^2 + \lambda \mathcal{R}(U)$$

where $d_u$ is the received data, S is the high-resolution coil sensitivity estimated from fully sampled data by combining $d_u$ along the time dimension, F and Ω denote the Fourier encoding in the spatial domain and under-sampling mask in k-t domain, respectively, V is the temporally global subspace, and U denotes the coefficient images to be reconstructed, i.e., image series in spatial and SVD compressed temporal domain, and wherein the aliasing-free and high-resolution time-resolved images $\hat{m}$ are generated by $\hat{U}V^H$.

11. The MRI system according to claim 2, wherein the at least one processor is further configured to generate a set of corrected high resolution images from the aliasing-free high resolution time-resolved images.

12. The MRI system according to claim 2, wherein the pulse sequence is a magnetic resonance fingerprinting (MRF) pulse sequence, the acquired data from the subject is MRF data and the aliasing-free high resolution time-resolved images are MRF images.

13. The MRI system according to claim 2, wherein the pulse sequence is a multidimensional magnetic resonance fingerprinting (mdMRF) pulse sequence, the acquired data from the subject is mdMRF data and the aliasing-free high resolution time-resolved images are mdMRF images.

14. The MRI system according to claim 2, wherein the at least a portion of the received data is a set of central k-space data extracted from the received data.

15. The MRI system according to claim 2, wherein the temporally local low-rank matrix completion comprises a model given by:

$$\hat{m}_c = \underset{m_c}{\operatorname{argmin}} \left\|\hat{d}_c - \Omega F S_c m_c\right\|_2^2 + \lambda_l \sum_{s=1}^{N_s} \|m_{c,s}\|_*$$

where $\hat{d}_c$ is a set of central k-space extracted from the received data, $S_c$ is the low-resolution coil sensitivity estimated from fully sampled data by combining $\hat{d}_c$ along the time dimension, F and Ω denote the Fourier encoding in the spatial domain and under-sampling mask in k-t domain, respectively, $m_c$ is the low-resolution image series (x-t domain) to be reconstructed, and $m_{c,s}$ is a portion of $m_c$ corresponding to s-th segment, $N_s$ is the number of segments and $\lambda_l$ is the regularization parameter.

16. The MRI system according to claim 2, wherein estimating the temporally global subspace using the aliasing-free low resolution images comprises performing singular value decomposition and truncation on the aliasing-free low resolution images.

17. The MRI system according to claim 2, wherein the temporally global subspace reconstruction comprises a model given by:

$$\hat{U} = \underset{U}{\operatorname{argmin}} \|d_u - \Omega F S U V^H\|_2^2 + \lambda \mathcal{R}(U)$$

where $d_u$ is the received data, S is the high-resolution coil sensitivity estimated from fully sampled data by combining $d_u$ along the time dimension, F and Ω denote the Fourier encoding in the spatial domain and under-sampling mask in k-t domain, respectively, V is the temporally global subspace, and U denotes the coefficient images to be reconstructed, i.e., image series in spatial and SVD compressed temporal domain, and wherein the aliasing-free and high-resolution time-resolved images $\hat{m}$ are generated by $\hat{U}V^H$.

18. The non-transitory computer readable medium according to claim 3, wherein the at least a portion of the received data is a set of central k-space data extracted from the received data.

19. The method according to claim 4, wherein generating a set of corrected high resolution images from the aliasing-free high resolution time-resolved images comprises:

detecting one or more corrupted segments in the aliasing free high resolution time-resolved images; and excluding the corrupted segments from the aliasing-free high resolution time-resolved images.

20. The MRI system according to claim 11, wherein generating a set of corrected high resolution images from the aliasing-free high resolution time-resolved images comprises:

detecting one or more corrupted segments in the aliasing free high resolution time-resolved images; and excluding the corrupted segments from the aliasing-free high resolution time-resolved images.

* * * * *